United States Patent
Tymianski et al.

(10) Patent No.: US 9,629,892 B2
(45) Date of Patent: Apr. 25, 2017

(54) TREATMENT OF PENETRATIVE INJURY TO THE BRAIN

(75) Inventors: Michael Tymianski, Toronto (CA); Peter S. Lu, Fremont, CA (US); Jonathan David Garman, Thornhill (CA)

(73) Assignee: NoNO Inc., Toronto (CA)

( * ) Notice: Subject to any disclaimer, the term of this patent is extended or adjusted under 35 U.S.C. 154(b) by 0 days.

(21) Appl. No.: 13/816,663

(22) PCT Filed: Aug. 12, 2011

(86) PCT No.: PCT/US2011/047667
§ 371 (c)(1),
(2), (4) Date: Apr. 26, 2013

(87) PCT Pub. No.: WO2012/021854
PCT Pub. Date: Feb. 16, 2012

(65) Prior Publication Data
US 2013/0267470 A1    Oct. 10, 2013

Related U.S. Application Data

(60) Provisional application No. 61/373,204, filed on Aug. 12, 2010.

(51) Int. Cl.
| | |
|---|---|
| *A61K 38/07* | (2006.01) |
| *A61K 38/08* | (2006.01) |
| *C07K 7/06* | (2006.01) |
| *A61K 47/48* | (2006.01) |
| *G01N 33/573* | (2006.01) |
| *G01N 33/68* | (2006.01) |
| *C12N 9/02* | (2006.01) |
| *A61K 38/17* | (2006.01) |

(52) U.S. Cl.
CPC .......... *A61K 38/07* (2013.01); *A61K 38/08* (2013.01); *A61K 38/1709* (2013.01); *A61K 38/1787* (2013.01); *A61K 47/48315* (2013.01); *C07K 7/06* (2013.01); *C12N 9/0075* (2013.01); *C12Y 114/13039* (2013.01); *G01N 33/573* (2013.01); *G01N 33/6872* (2013.01); *C07K 2319/10* (2013.01); *G01N 2333/70571* (2013.01); *G01N 2333/90254* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 2005/0059597 A1* | 3/2005 | Tymianski | 514/12 |
| 2006/0148711 A1 | 7/2006 | Lu et al. | |
| 2007/0020717 A1* | 1/2007 | Belmares | C12Q 1/26 435/25 |
| 2007/0298009 A1* | 12/2007 | Gluckman et al. | 424/85.2 |
| 2008/0274977 A1* | 11/2008 | Belmares | C07K 14/70571 514/17.7 |
| 2009/0062213 A1* | 3/2009 | Belmares | A61K 38/06 514/1.1 |
| 2009/0176713 A1* | 7/2009 | Tymianski | A61K 9/0019 514/1.1 |
| 2009/0281036 A1 | 11/2009 | Meyer | |

FOREIGN PATENT DOCUMENTS

| | | |
|---|---|---|
| WO | WO 2009/006611 A1 | 1/2009 |
| WO | WO 2012/021854 A2 | 2/2012 |

OTHER PUBLICATIONS

Williams et al. 2006 "Penetrating Ballistic-like brain injury in the rat: differential time courses of hemorrhage, cell death, inflammation, and remote degeneration" J Neurotrauma 23(12):1828-1846.*
Menniti 1998 "CP-101,606: an nr2b-selective nmda receptor antagonist" CNS drug reviews 4(4):307-322.*
Cui et al., "PDZ Protein Interactions Underlying NMDA Receptor-Mediated Excitotoxicity and Neuroprotection by PSD-95 Inhibitors," J Neurosci., 27(37):9901-9915, (2007).
Lim et al., "Disruption of the NMDA receptor-PSD-95 interaction in hippocampal neurons with no obvious physiological short-term effect," Neuropharmacology, 45:738-754, (2003).
EPO Application No. 11817146.1 (EP2616094), EPO Supplementary European Search Report and European Search Opinion mailed Apr. 11, 2014.
WIPO Application No. PCT/US2011/047667, PCT International Preliminary Report on Patentability issued Feb. 12, 2013.
WIPO Application No. PCT/US2011/047667, PCT International Search Report mailed Mar. 28, 2012.
WIPO Application No. PCT/US2011/047667, PCT Written Opinion of the International Searching Authority mailed Mar. 28, 2012.

\* cited by examiner

*Primary Examiner* — Adam M Weidner
(74) *Attorney, Agent, or Firm* — Alston & Bird LLP

(57) ABSTRACT

The invention provides methods of treatment or prophylaxis of damaging effects of penetrative injury to the brain or other part of the central nervous system. The methods are based in part on results in a rodent model of penetrative ballistic injury showing that an inhibitor of PDF-95 NMDAR interaction is effective in inhibiting neurological deficits resulting from such injury. The methods are useful for treating subjects having or at risk of penetrative brain injury, including subjects who have been shot in the head or at risk of such injury (e.g., military or law enforcement personnel).

18 Claims, 12 Drawing Sheets

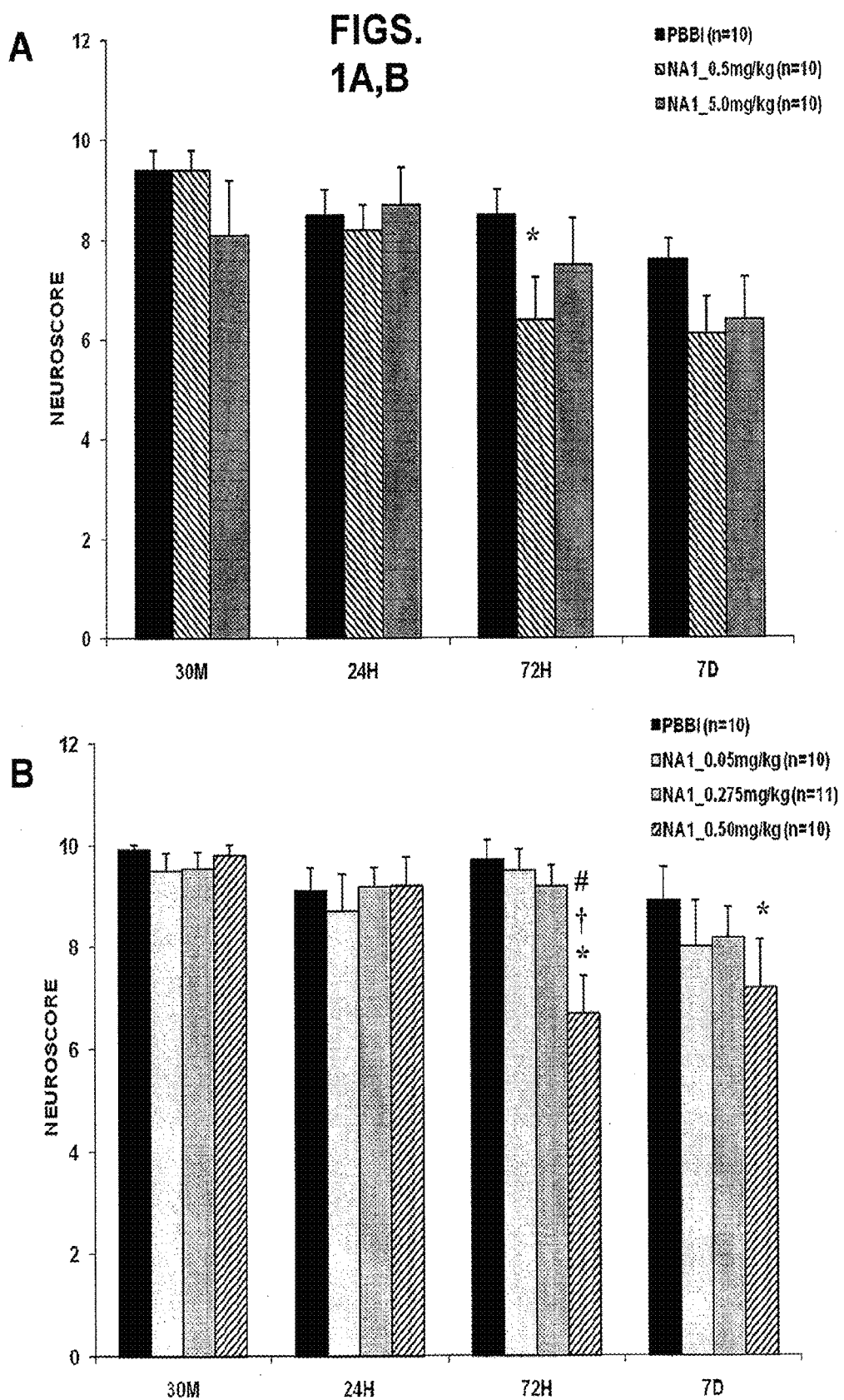
FIGS. 1A,B

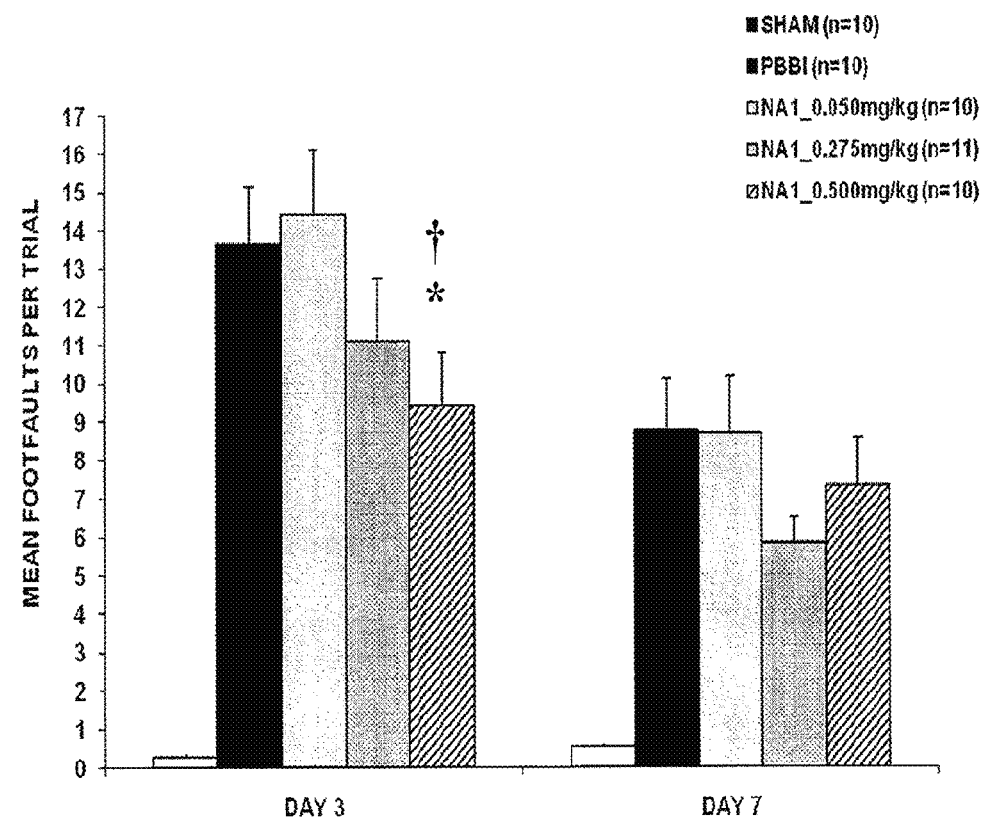

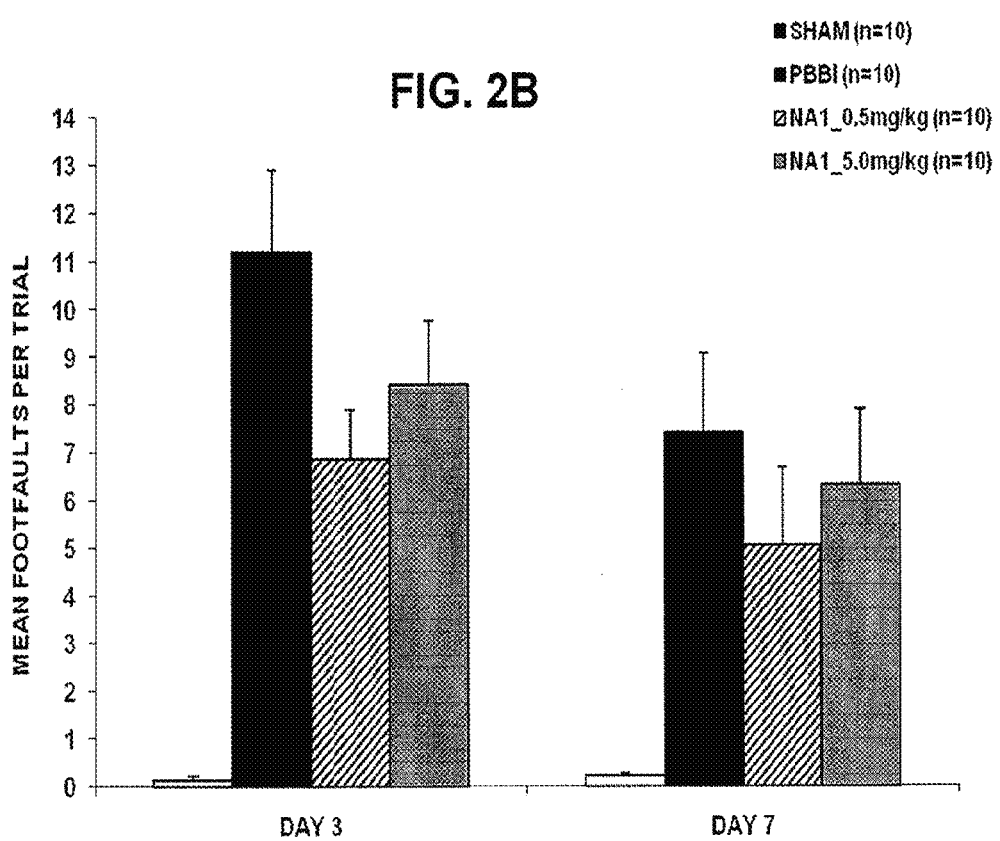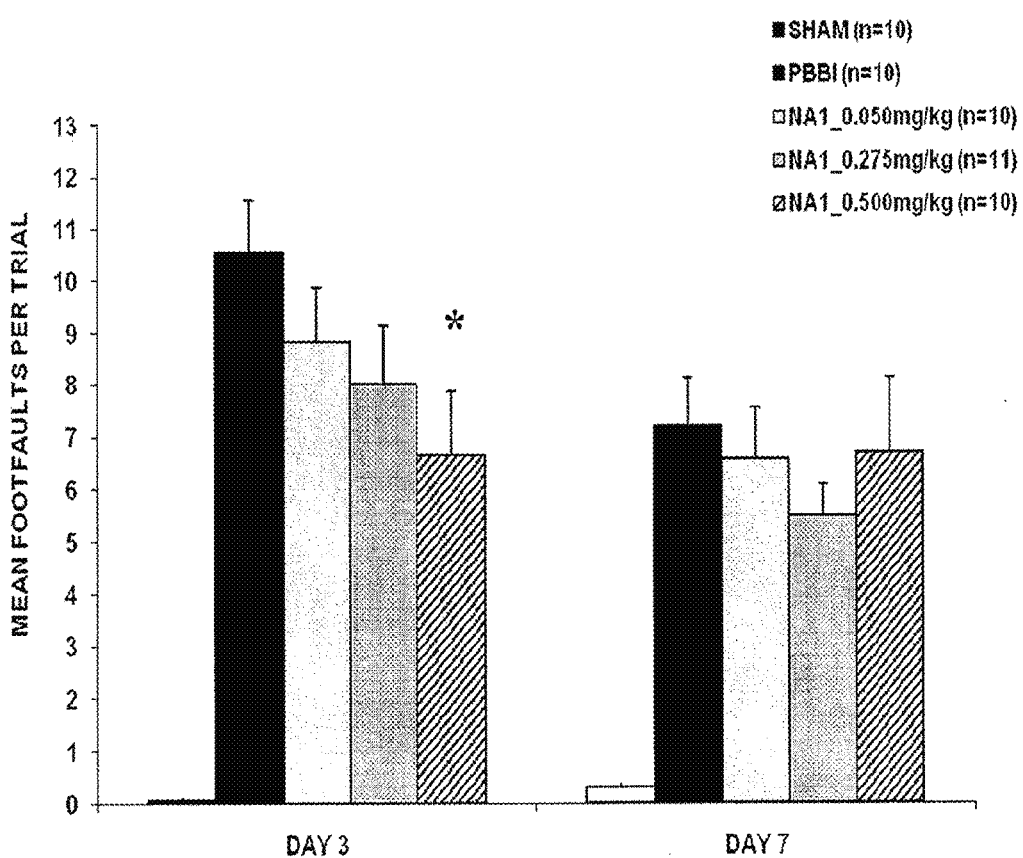
FIG. 2B

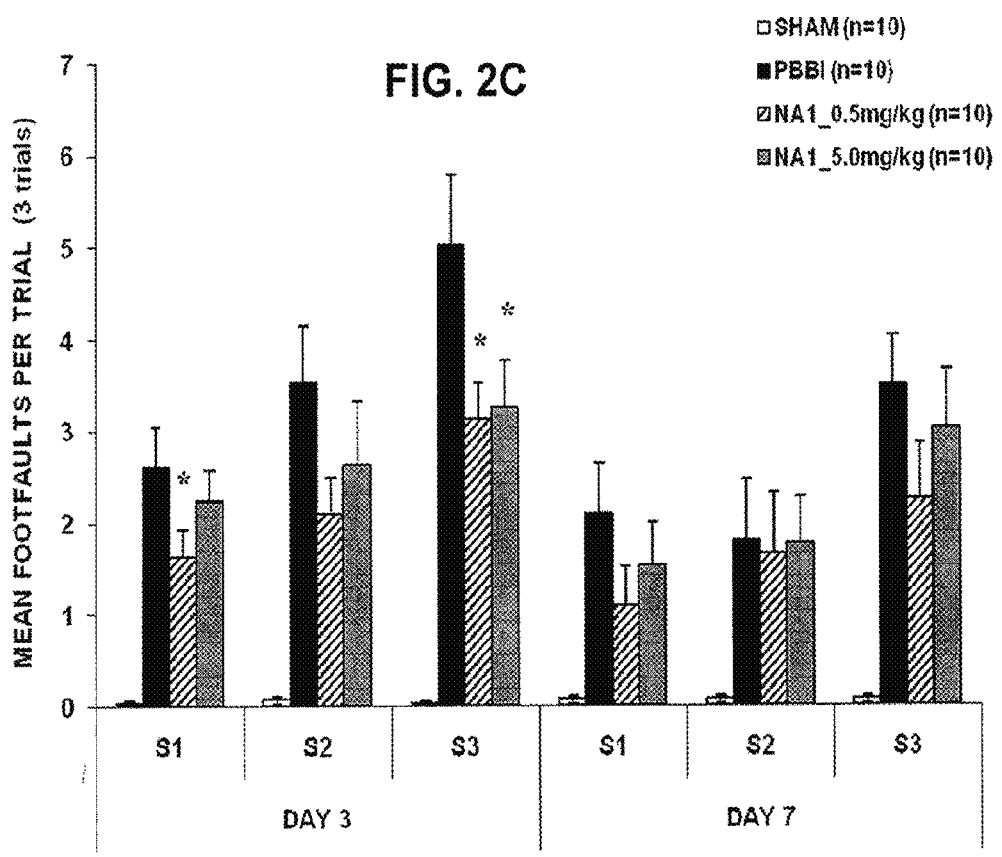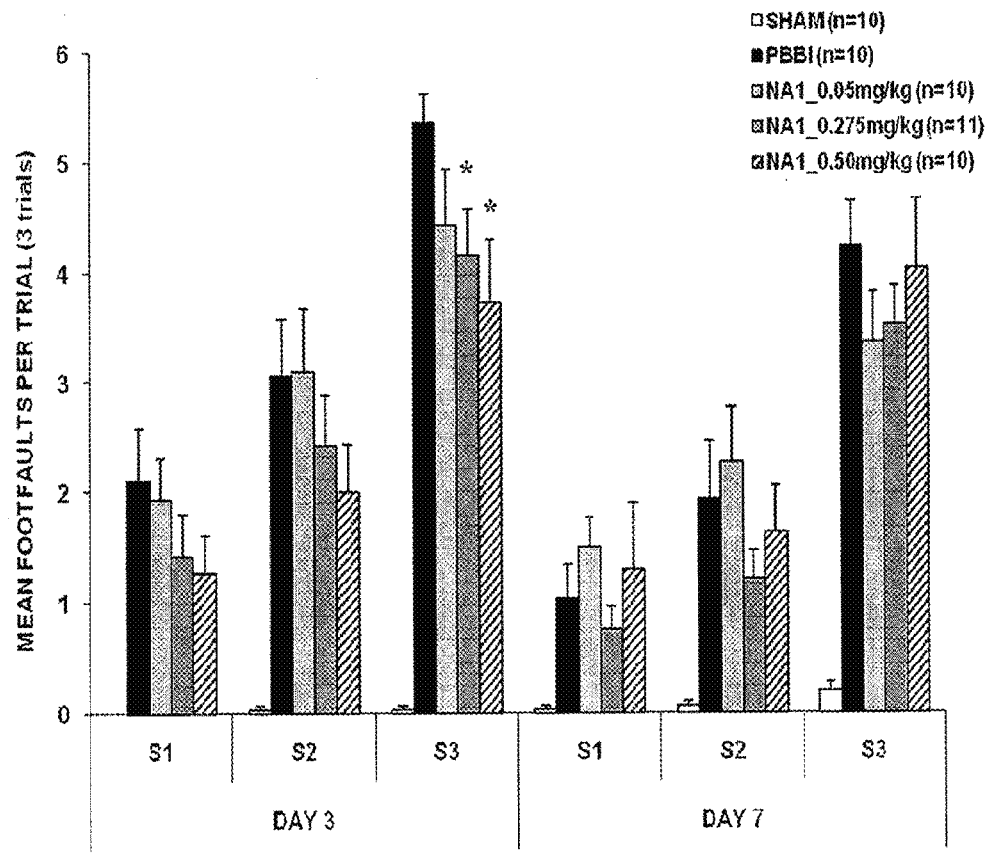

FIGS. 3A, B
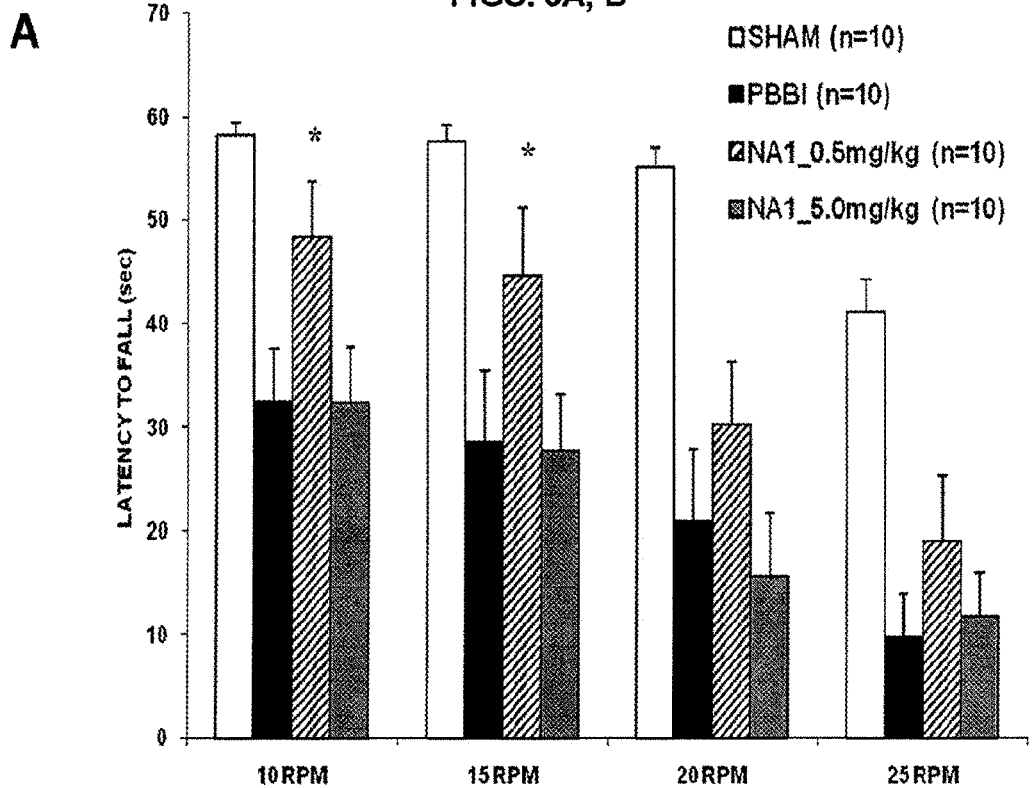
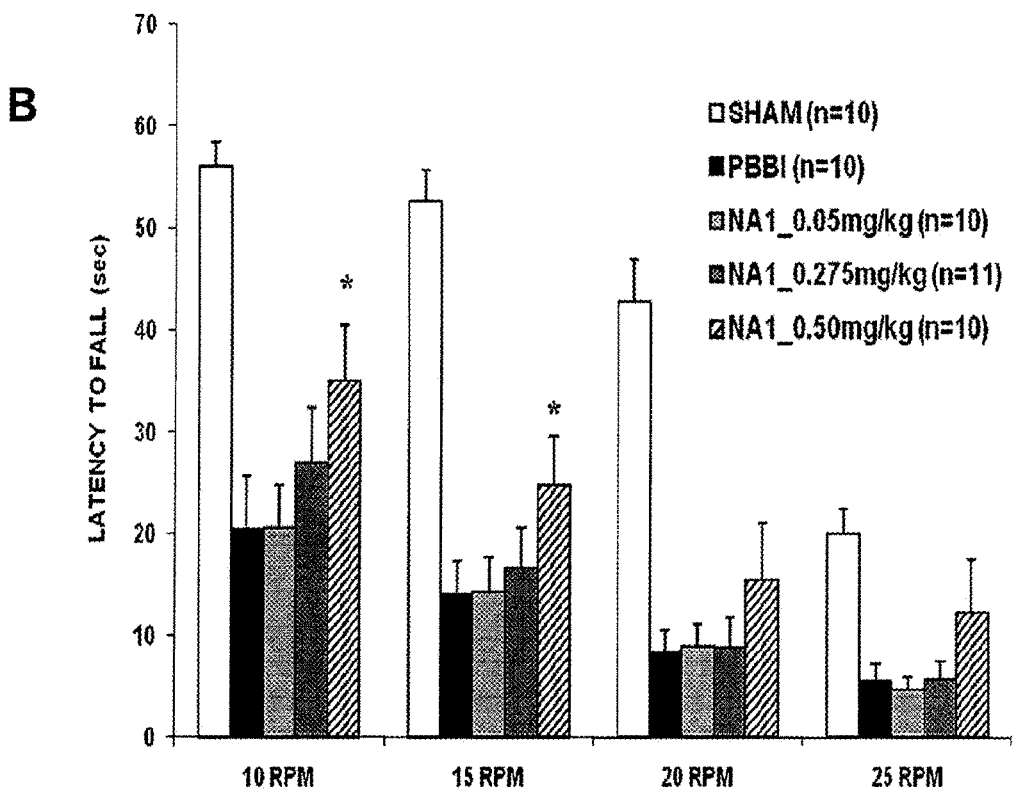

FIGS. 4A, B (left)
A. LESION VOLUME
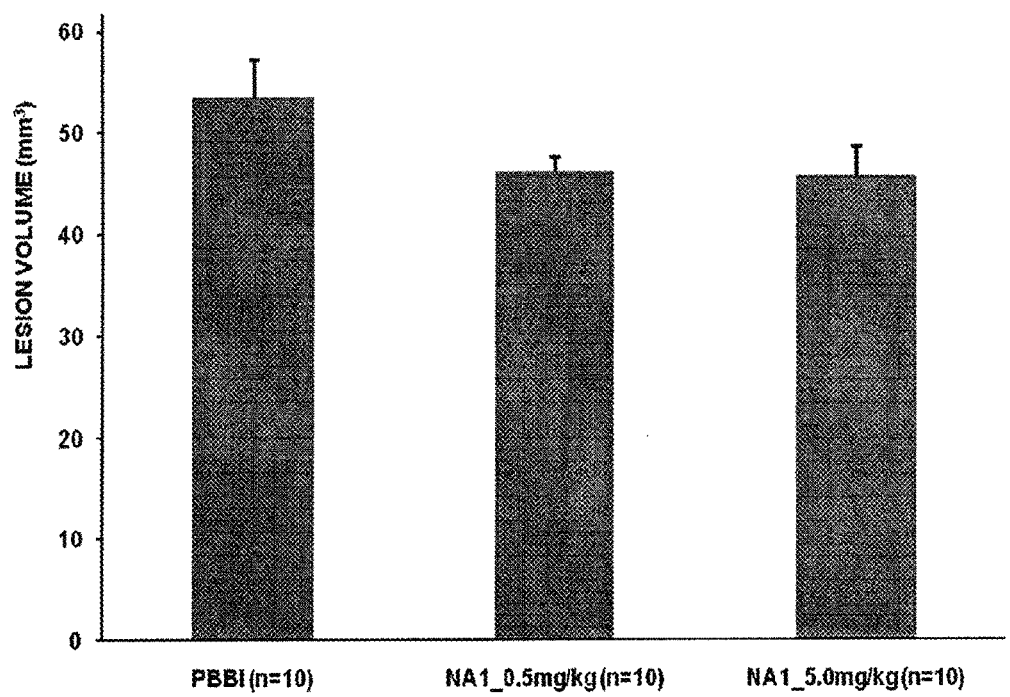
B. LESION PROGRESSION
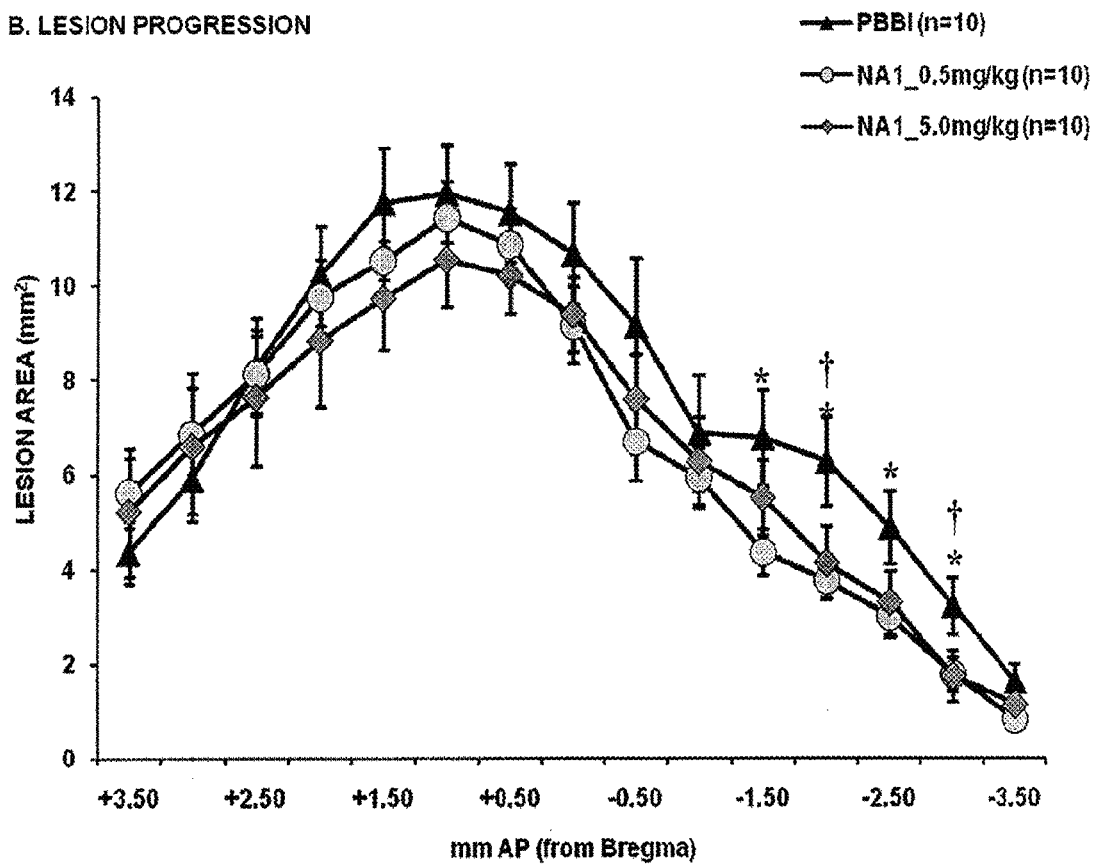

FIG. 4B (right)
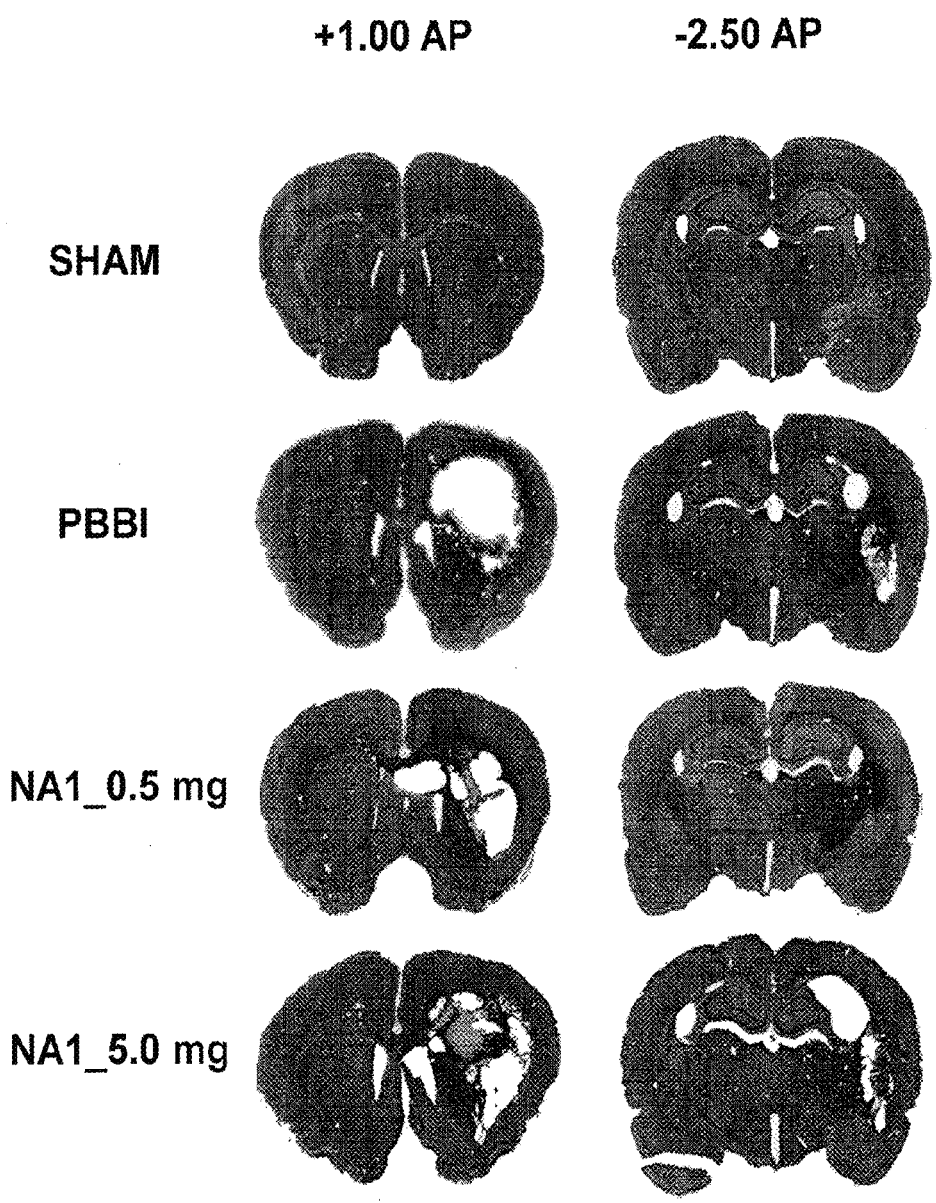

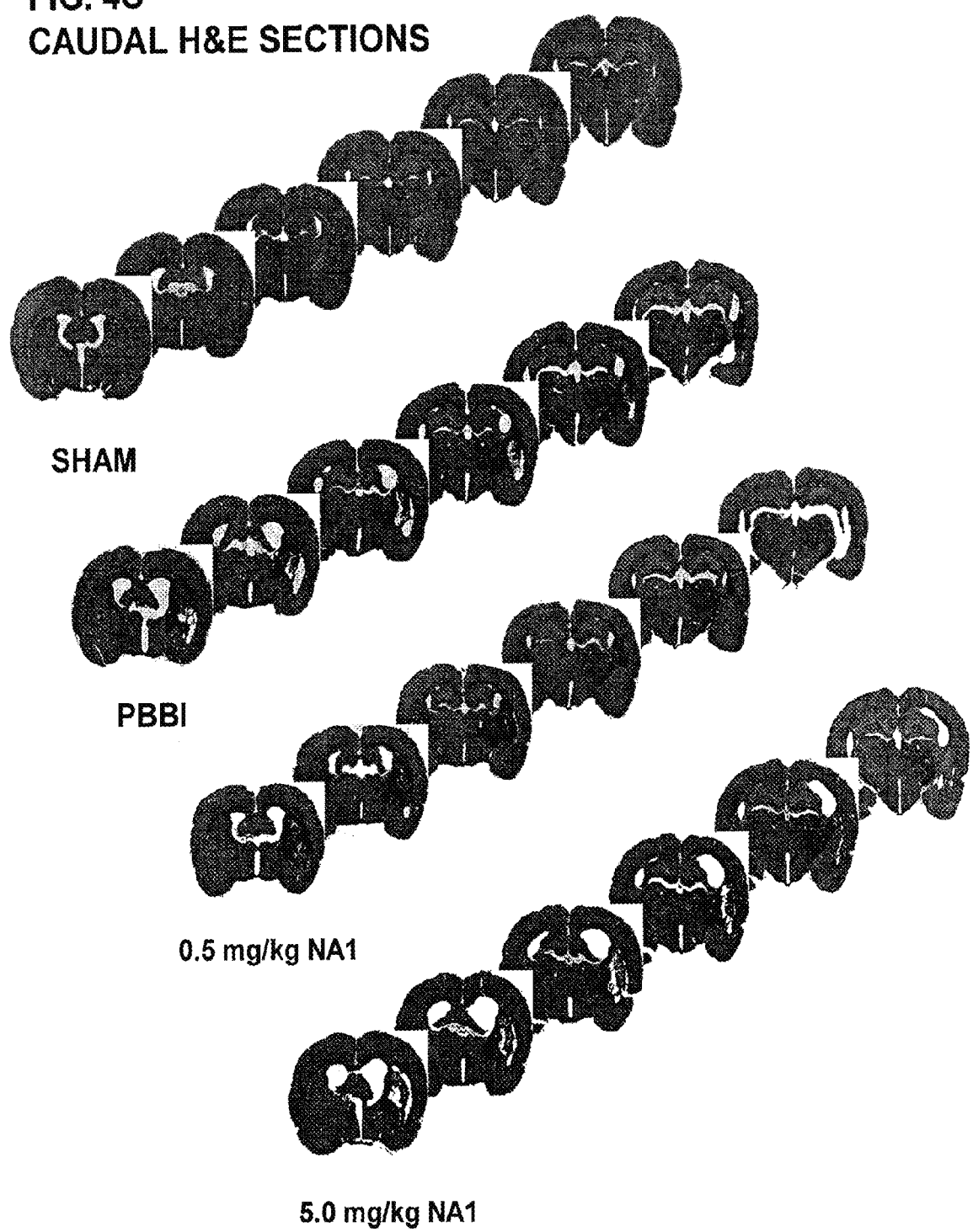

FIGS. 5A, B
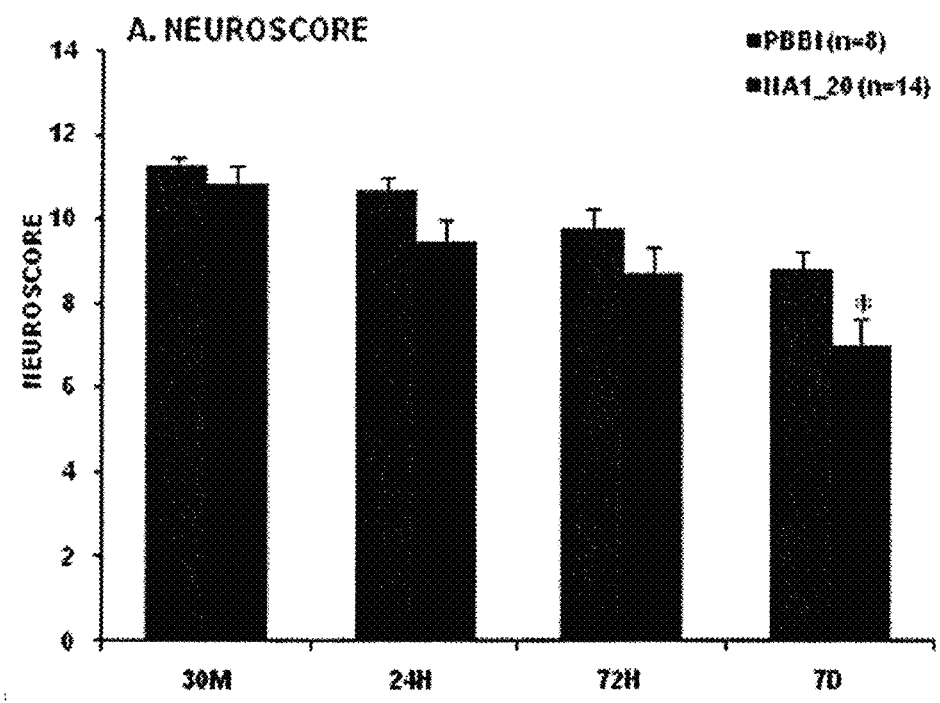
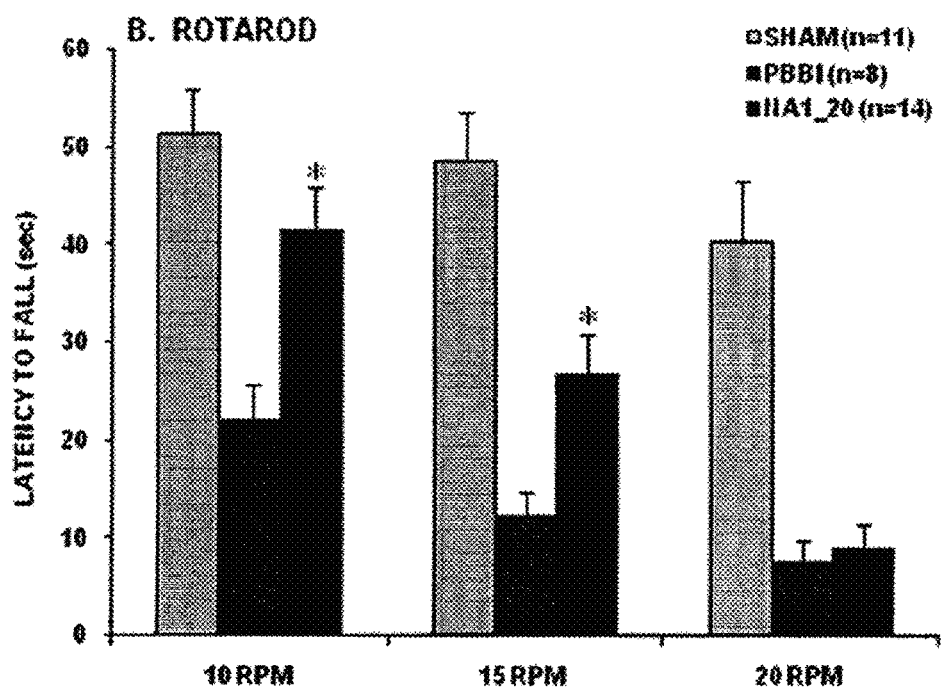

FIGS. 5 C,D
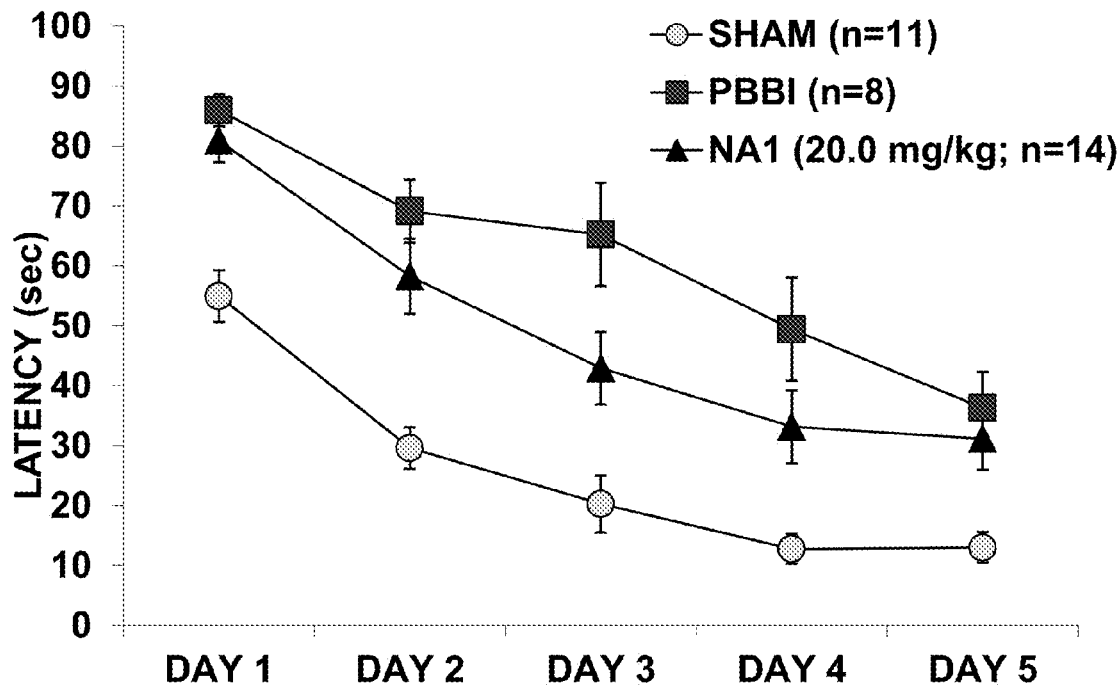
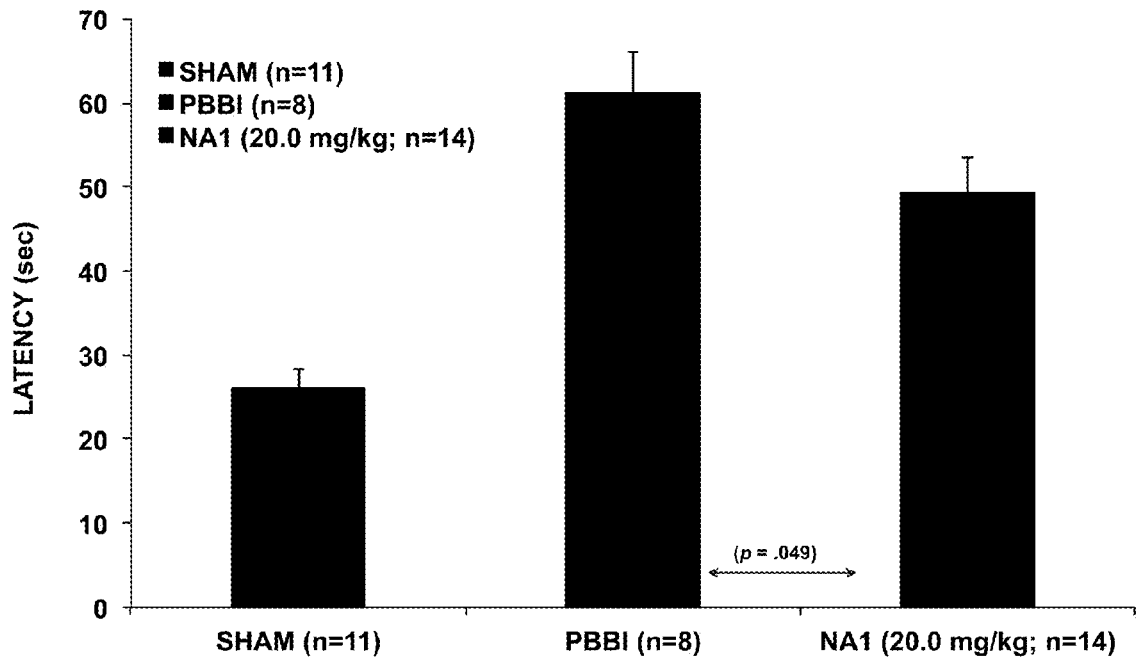

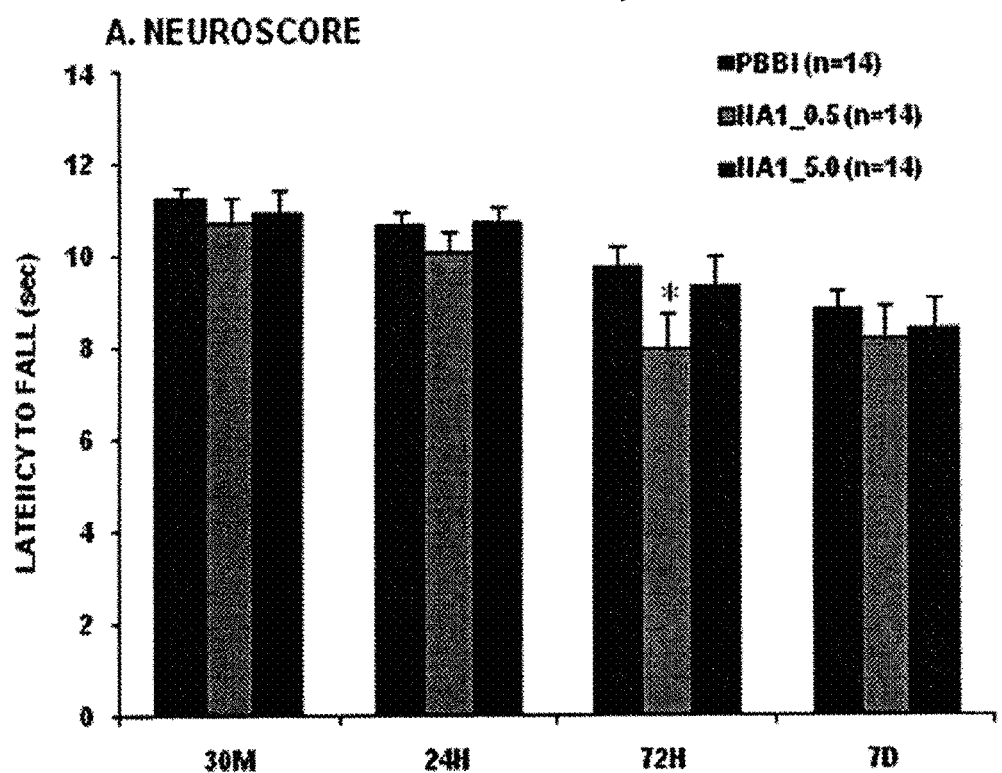
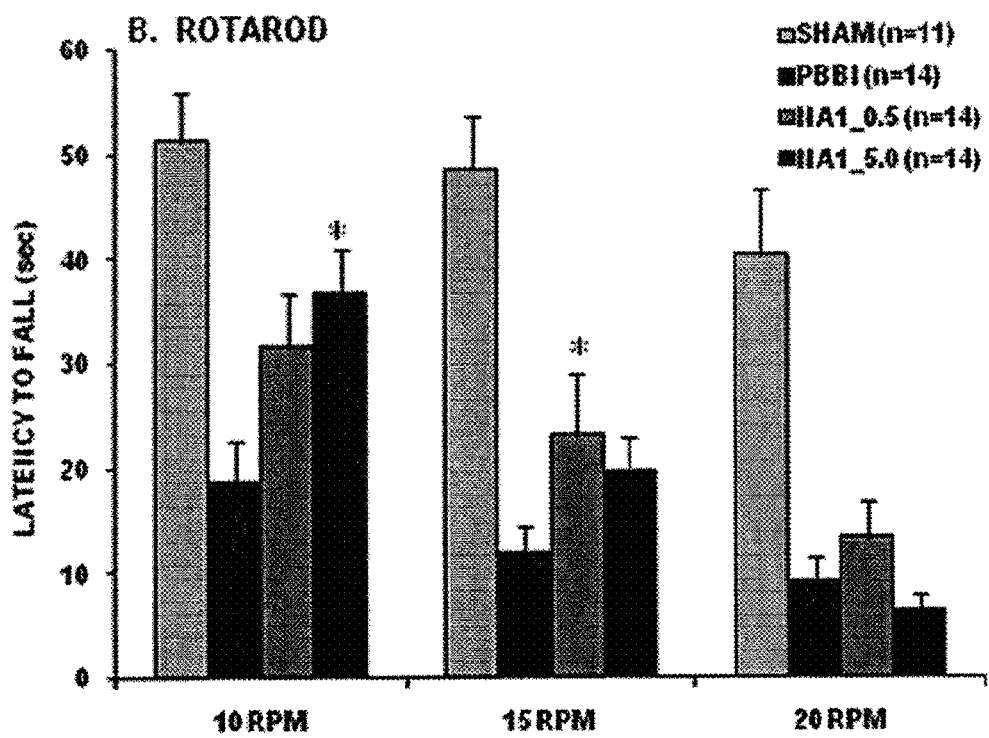
FIGS. 6A, B

FIGS. 6 C,D
C. MWM – DAILY MEAN LATENCY
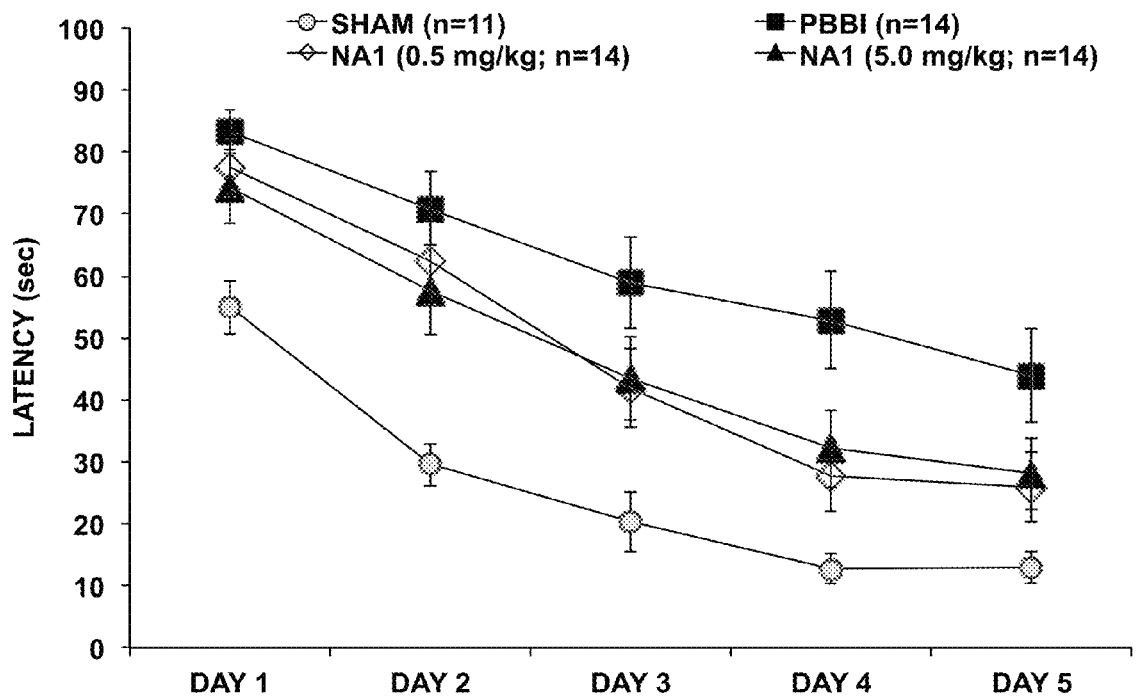
D. MWM – TOTAL MEAN LATENCY
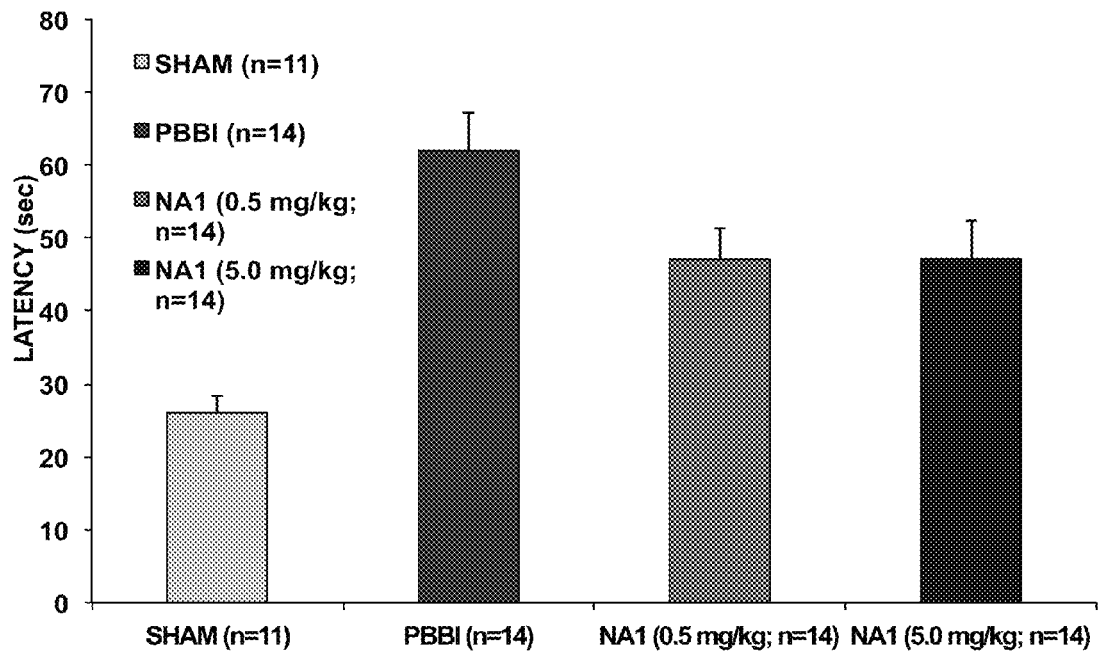

SEQUENCE LISTING

```
<160> NUMBER OF SEQ ID NOS: 69

<210> SEQ ID NO 1
<211> LENGTH: 10
<212> TYPE: PRT
<213> ORGANISM: Human immunodeficiency virus

<400> SEQUENCE: 1

Gly Arg Lys Lys Arg Arg Gln Arg Arg Arg
1               5                   10

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg Arg
1               5                   10

<210> SEQ ID NO 3
<211> LENGTH: 11
<212> TYPE: PRT
<213> ORGANISM: Human immunodeficiency virus

<400> SEQUENCE: 3

Phe Gly Arg Lys Lys Arg Arg Gln Arg Arg Arg
1               5                   10

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Asp Ser Glu Ile Ser Ser Leu Lys Arg Arg Gln Arg Arg Lys
1               5                   10                  15

Lys Arg Gly Tyr Ile Asn
            20

<210> SEQ ID NO 5
<211> LENGTH: 9
<212> TYPE: PRT
<213> ORGANISM: Homo sapiens

<400> SEQUENCE: 5

Lys Leu Ser Ser Ile Glu Ser Asp Val
1               5

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Arg Arg Arg Gln Arg Arg Lys Lys Arg Gly Tyr Lys Leu Ser Ser Ile
1               5                   10                  15

Glu Ser Asp Val
            20

<210> SEQ ID NO 7
<211> LENGTH: 4
<212> TYPE: PRT
<213> ORGANISM: Unknown
<220> FEATURE:
<223> OTHER INFORMATION: Description of Unknown: PDZ domain
      "GLGF" repeat peptide sequence

<400> SEQUENCE: 7

Gly Leu Gly Phe
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, Gln, or Ala
<220> FEATURE:
<221> NAME/KEY: MOD_RES
<222> LOCATION: (2)..(2)
<223> OTHER INFORMATION: Thr or Ser
<220> FEATURE:
<221> NAME/KEY: MOD_RES
<222> LOCATION: (3)..(3)
<223> OTHER INFORMATION: Ala, Gln, Asp, Asn, N-Me-Ala, N-Me-Gln,
      N-Me-Asp, or N-Me-Asn
<220> FEATURE:
<223> OTHER INFORMATION: see specification as filed for detailed
      description of substitutions and preferred embodiments

<400> SEQUENCE: 8

Xaa Xaa Xaa Val
1

<210> SEQ ID NO 9
<211> LENGTH: 5
<212> TYPE: PRT
<213> ORGANISM: Homo sapiens

<400> SEQUENCE: 9

Ile Glu Ser Asp Val
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments
```

```
<400> SEQUENCE: 10

Xaa Phe Gly Arg Lys Lys Arg Arg Gln Arg Arg Arg
1               5                   10

<210> SEQ ID NO 11
<211> LENGTH: 20
<212> TYPE: PRT
<213> ORGANISM: Homo sapiens

<400> SEQUENCE: 11

Phe Asn Gly Ser Ser Asn Gly His Val Tyr Glu Lys Leu Ser Ser Ile
1               5                   10                  15

Glu Ser Asp Val
            20

<210> SEQ ID NO 12
<211> LENGTH: 4
<212> TYPE: PRT
<213> ORGANISM: Homo sapiens

<400> SEQUENCE: 12

Glu Ser Asp Val
1

<210> SEQ ID NO 13
<211> LENGTH: 20
<212> TYPE: PRT
<213> ORGANISM: Homo sapiens

<400> SEQUENCE: 13

His Pro Thr Asp Ile Thr Gly Pro Leu Asn Leu Ser Asp Pro Ser Val
1               5                   10                  15

Ser Thr Val Val
            20

<210> SEQ ID NO 14
<211> LENGTH: 20
<212> TYPE: PRT
<213> ORGANISM: Homo sapiens

<400> SEQUENCE: 14

Arg Arg Ala Ile Glu Arg Glu Glu Gly Gln Leu Gln Leu Cys Ser Arg
1               5                   10                  15

His Arg Glu Ser
            20

<210> SEQ ID NO 15
<211> LENGTH: 20
<212> TYPE: PRT
<213> ORGANISM: Homo sapiens

<400> SEQUENCE: 15

Thr Gln Gly Phe Pro Gly Pro Cys Thr Trp Arg Arg Ile Ser Ser Leu
1               5                   10                  15

Glu Ser Glu Val
            20

<210> SEQ ID NO 16
<211> LENGTH: 20
<212> TYPE: PRT
<213> ORGANISM: Homo sapiens
```

```
<400> SEQUENCE: 16

Ala Val Ser Arg Lys Thr Glu Leu Glu Glu Tyr Gln Arg Thr Ser Arg
1               5                   10                  15

Thr Cys Glu Ser
            20

<210> SEQ ID NO 17
<211> LENGTH: 20
<212> TYPE: PRT
<213> ORGANISM: Homo sapiens

<400> SEQUENCE: 17

Leu Asn Ser Cys Ser Asn Arg Arg Val Tyr Lys Lys Met Pro Ser Ile
1               5                   10                  15

Glu Ser Asp Val
            20

<210> SEQ ID NO 18
<211> LENGTH: 20
<212> TYPE: PRT
<213> ORGANISM: Homo sapiens

<400> SEQUENCE: 18

Gly Gly Asp Leu Gly Thr Arg Arg Gly Ser Ala His Phe Ser Ser Leu
1               5                   10                  15

Glu Ser Glu Val
            20

<210> SEQ ID NO 19
<211> LENGTH: 20
<212> TYPE: PRT
<213> ORGANISM: Homo sapiens

<400> SEQUENCE: 19

Gln Pro Thr Pro Thr Leu Gly Leu Asn Leu Gly Asn Asp Pro Asp Arg
1               5                   10                  15

Gly Thr Ser Ile
            20

<210> SEQ ID NO 20
<211> LENGTH: 20
<212> TYPE: PRT
<213> ORGANISM: Homo sapiens

<400> SEQUENCE: 20

Met Gln Ser Ile Pro Cys Met Ser His Ser Ser Gly Met Pro Leu Gly
1               5                   10                  15

Ala Thr Gly Leu
            20

<210> SEQ ID NO 21
<211> LENGTH: 20
<212> TYPE: PRT
<213> ORGANISM: Homo sapiens

<400> SEQUENCE: 21

Gln Asn Phe Ala Thr Tyr Lys Glu Gly Tyr Asn Val Tyr Gly Ile Glu
1               5                   10                  15

Ser Val Lys Ile
            20
```

-continued

```
<210> SEQ ID NO 22
<211> LENGTH: 20
<212> TYPE: PRT
<213> ORGANISM: Homo sapiens

<400> SEQUENCE: 22

Gln Asn Tyr Ala Thr Tyr Arg Glu Gly Tyr Asn Val Tyr Gly Thr Glu
1               5                   10                  15

Ser Val Lys Ile
            20

<210> SEQ ID NO 23
<211> LENGTH: 20
<212> TYPE: PRT
<213> ORGANISM: Homo sapiens

<400> SEQUENCE: 23

His Thr Gly Thr Ala Ile Arg Gln Ser Ser Gly Leu Ala Val Ile Ala
1               5                   10                  15

Ser Asp Leu Pro
            20

<210> SEQ ID NO 24
<211> LENGTH: 20
<212> TYPE: PRT
<213> ORGANISM: Homo sapiens

<400> SEQUENCE: 24

Ser Phe Thr Ser Ile Leu Thr Cys His Gln Arg Arg Thr Gln Arg Lys
1               5                   10                  15

Glu Thr Val Ala
            20

<210> SEQ ID NO 25
<211> LENGTH: 20
<212> TYPE: PRT
<213> ORGANISM: Homo sapiens

<400> SEQUENCE: 25

Glu Val Ile Asn Met His Thr Phe Asn Asp Arg Arg Leu Pro Gly Lys
1               5                   10                  15

Glu Thr Met Ala
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Gly Arg Lys Lys Arg Arg Gln Arg Arg Lys Leu Ser Ser Ile
1               5                   10                  15

Glu Ser Asp Val
            20

<210> SEQ ID NO 27
<211> LENGTH: 4
<212> TYPE: PRT
<213> ORGANISM: Homo sapiens

<400> SEQUENCE: 27
```

Ser Thr Val Val
1

<210> SEQ ID NO 28
<211> LENGTH: 4
<212> TYPE: PRT
<213> ORGANISM: Homo sapiens

<400> SEQUENCE: 28

His Arg Glu Ser
1

<210> SEQ ID NO 29
<211> LENGTH: 4
<212> TYPE: PRT
<213> ORGANISM: Homo sapiens

<400> SEQUENCE: 29

Glu Ser Glu Val
1

<210> SEQ ID NO 30
<211> LENGTH: 4
<212> TYPE: PRT
<213> ORGANISM: Homo sapiens

<400> SEQUENCE: 30

Thr Cys Glu Ser
1

<210> SEQ ID NO 31
<211> LENGTH: 4
<212> TYPE: PRT
<213> ORGANISM: Homo sapiens

<400> SEQUENCE: 31

Gly Thr Ser Ile
1

<210> SEQ ID NO 32
<211> LENGTH: 4
<212> TYPE: PRT
<213> ORGANISM: Homo sapiens

<400> SEQUENCE: 32

Ala Thr Gly Leu
1

<210> SEQ ID NO 33
<211> LENGTH: 4
<212> TYPE: PRT
<213> ORGANISM: Homo sapiens

<400> SEQUENCE: 33

Ser Val Lys Ile
1

<210> SEQ ID NO 34
<211> LENGTH: 4
<212> TYPE: PRT
<213> ORGANISM: Homo sapiens

<400> SEQUENCE: 34

Ser Asp Leu Pro

```
<210> SEQ ID NO 35
<211> LENGTH: 4
<212> TYPE: PRT
<213> ORGANISM: Homo sapiens

<400> SEQUENCE: 35

Glu Thr Val Ala
1

<210> SEQ ID NO 36
<211> LENGTH: 4
<212> TYPE: PRT
<213> ORGANISM: Homo sapiens

<400> SEQUENCE: 36

Glu Thr Met Ala
1

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Gly Tyr Lys Lys Arg Arg Gln Arg Arg Arg Lys Leu Ser Ser Ile
1               5                   10                  15

Glu Ser Asp Val
            20

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Glu, Asp, Asn or Gln
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Asp, Glu, Gln or Asn
<220> FEATURE:
<221> NAME/KEY: MOD_RES
<222> LOCATION: (4)..(4)
<223> OTHER INFORMATION: Val or Leu

<400> SEQUENCE: 38

Xaa Xaa Xaa Xaa
1

<210> SEQ ID NO 39
<211> LENGTH: 4
<212> TYPE: PRT
<213> ORGANISM: Homo sapiens

<400> SEQUENCE: 39
```

```
Glu Thr Asp Val
1

<210> SEQ ID NO 40
<211> LENGTH: 4
<212> TYPE: PRT
<213> ORGANISM: Homo sapiens

<400> SEQUENCE: 40

Glu Thr Glu Val
1

<210> SEQ ID NO 41
<211> LENGTH: 4
<212> TYPE: PRT
<213> ORGANISM: Homo sapiens

<400> SEQUENCE: 41

Asp Thr Asp Val
1

<210> SEQ ID NO 42
<211> LENGTH: 4
<212> TYPE: PRT
<213> ORGANISM: Homo sapiens

<400> SEQUENCE: 42

Asp Thr Glu Val
1

<210> SEQ ID NO 43
<211> LENGTH: 9
<212> TYPE: PRT
<213> ORGANISM: Homo sapiens

<400> SEQUENCE: 43

Lys Leu Ser Ser Ile Glu Thr Asp Val
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ser Ser Ser Ser
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Gly Glu Lys Pro
1               5

<210> SEQ ID NO 46
<211> LENGTH: 8
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 46

Gly Gly Arg Arg Gly Gly Gly Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Arg Gln Arg Asp Gly Glu Arg Pro
1               5

<210> SEQ ID NO 48
<211> LENGTH: 13
<212> TYPE: PRT
<213> ORGANISM: Human immunodeficiency virus

<400> SEQUENCE: 48

Tyr Gly Arg Lys Lys Arg Arg Gln Arg Arg Pro Gln
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Tyr or absent

<400> SEQUENCE: 49

Xaa Gly Arg Lys Lys Arg Arg Gln Arg Arg Arg
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 50

Xaa Gly Lys Lys Lys Lys Lys Gln Lys Lys Lys
1               5                   10

<210> SEQ ID NO 51
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 51

Xaa Arg Lys Lys Arg Arg Gln Arg Arg Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 52

Xaa Gly Ala Lys Lys Arg Arg Gln Arg Arg Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 53

Xaa Ala Lys Lys Arg Arg Gln Arg Arg Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 54

Xaa Gly Arg Lys Ala Arg Arg Gln Arg Arg Arg
1               5                   10
```

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 55

Xaa Arg Lys Ala Arg Arg Gln Arg Arg Arg
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 56

Xaa Gly Arg Lys Lys Ala Arg Gln Arg Arg Arg
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 57

Xaa Arg Lys Lys Ala Arg Gln Arg Arg Arg
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 58

Xaa Gly Arg Lys Lys Arg Arg Gln Ala Arg Arg
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 59

Xaa Arg Lys Lys Arg Arg Gln Ala Arg Arg
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 60

Xaa Gly Arg Lys Lys Arg Arg Gln Arg Ala Arg
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 61

Xaa Arg Lys Lys Arg Arg Gln Arg Ala Arg
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Any amino acid or absent
<220> FEATURE:
<223> OTHER INFORMATION: see specification as filed for detailed
      description of substitutions and preferred embodiments

<400> SEQUENCE: 62

Xaa Arg Arg Pro Arg Arg Pro Arg Arg Pro Arg Arg
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 63

Xaa Arg Arg Ala Arg Arg Ala Arg Arg Ala Arg Arg
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 64

Xaa Arg Arg Arg Ala Arg Arg Arg Ala Arg Arg
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 65

Xaa Arg Arg Arg Pro Arg Arg Arg Pro Arg Arg
1               5                   10

<210> SEQ ID NO 66
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 66

Xaa Arg Arg Pro Arg Arg Pro Arg Arg
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<223> OTHER INFORMATION: see specification as filed for detailed
      description of substitutions and preferred embodiments

<400> SEQUENCE: 67

Xaa Arg Arg Ala Arg Arg Ala Arg Arg
1               5

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe Gly Tyr Lys Lys Arg Arg Gln Arg Arg Lys Leu Ser Ser Ile
1               5                   10                  15

Glu Thr Asp Val
            20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Gly Arg Lys Lys Arg Arg Gln Arg Arg Lys Leu Ser Ser Ile
1               5                   10                  15

Glu Thr Asp Val
            20
```

TREATMENT OF PENETRATIVE INJURY TO THE BRAIN

CROSS-REFERENCE TO RELATED APPLICATIONS

This application is the US national stage of PCT/US2011/047667 filed Aug. 12, 2011, which is a non-provisional and claims the benefit of 61/373,204, filed Aug. 12, 2010.

REFERENCE TO A SEQUENCE LISTING

This application includes an electronic sequence listing in a file named "429664SEQLISTCORRECTED.txt created on May 28, 2013, and having a size of 18 kilobytes. The information in this file is hereby incorporated by reference.

BACKGROUND OF THE INVENTION

Glutamate is the main excitatory neurotransmitter in the central nervous system (CNS) and mediates neurotransmission across most excitatory synapses. Three classes of glutamate-gated ion channel receptors (N-methyl-D-aspartate (NMDA), alpha-amino-3-hydroxy-5-methylisoxazole-4-propionic acid (AMPA) and Kainate) transduce the post-synaptic signal. Of these, NMDA receptors (NMDAR) are responsible for a significant portion of the excitotoxicity of glutamate. NMDA receptors are complex having an NR1 subunit and one or more NR2 subunits (2A, 2B, 2C or 2D) (see, e.g., McDain, C. and Caner, M. (1994) Physiol. Rev. 74:723-760), and less commonly, an NR3 subunit (Chatterton et al. (2002) Nature 415:793-798). The NR1 subunits have been shown to bind glycine, whereas NR2 subunits bind glutamate. Both glycine and glutamate binding are required to open the ion channel and allow calcium entry into the cell. The four NR2 receptor subunits appear to determine the pharmacology and properties of NMDA receptors, with further contributions from alternative splicing of the NR1 subunit (Kornau et al. (1995) Science 269:1737-40). Whereas NR1 and NR2A subunits are ubiquitously expressed in the brain, NR2B expression is restricted to the forebrain, NR2C to the cerebellum, and NR2D is rare compared to the other types.

Because of the key role of NMDA receptors in the excitotoxicity response, they have been considered as targets for therapeutics. Compounds have been developed that target the ion channel (ketamine, phencyclidine, PCP, MK801, amantadine), the outer channel (magnesium), the glycine binding site on NR1 subunits, the glutamate binding site on NR2 subunits, and specific sites on NR2 subunits (Zinc—NR2A; Ifenprodil, Traxoprodil—NR2B). Among these, the non-selective antagonists of NMDA receptor have been the most neuroprotective agents in animal models of stroke. However, clinical trials with these drugs in stroke and traumatic brain injury have so far failed, generally as a result of severe side effects such as hallucination and even coma.

Postsynaptic density-95 protein (PSD-95) couples NMDARs to pathways mediating excitotoxicity and ischemic brain damage (Aarts et al., Science 298, 846-850 (2002)). This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults and reduced cerebral infarction volume in rats subjected to transient focal cerebral ischemia. Treatment was also reported to be protective in a rat model of fluid percussion injury in which a fluid volume is rapidly injected into the cranial cavity (see US 20050059597). The injury in such a model has a mild primary effect in terms of immediate tissue damage but extensive secondary effects results from excitotoxicity.

SUMMARY OF THE CLAIMED INVENTION

The invention provides methods of treating or effecting prophylaxis of a damaging effect of penetrative injury to the CNS, comprising administering to a subject having or at risk of penetrative injury to the CNS a pharmacological agent that inhibits binding of PSD-95 to an NMDAR and/or of PSD-95 to nNOS. In some methods, the subject has a gunshot wound in the head, or a penetrative wound from a sharp object in the head, such as a knife. In some methods, the subject is a military or law enforcement person at risk of being shot. In some methods, the subject is free of and/or not at risk of other disease amenable to treatment with the pharmacological agent. In some methods, the subject has a penetrative injury and the administering inhibits development of neurological deficits in the subject. In some methods, the pharmacological agent comprises a peptide having an amino acid sequence comprising T/SXV/L linked to an internalization peptide.

In some methods, the pharmacological agent comprises a peptide having an amino acid sequence comprising [E/D/N/Q]-[S/T/H/D/E/Q/N]-[V/L] (SEQ ID NO: 38) linked to an internalization peptide. In some methods, the pharmacological agent comprises a peptide having an amino acid sequence comprising ESDV (SEQ ID NO: 12), ESEV (SEQ ID NO: 29), ETDV (SEQ ID NO: 39), ETEV (SEQ ID NO: 40), DTDV (SEQ ID NO: 41), or DTEV (SEQ ID NO: 42) linked to an internalization peptide. In some methods, the pharmacological agent has an amino acid sequence comprising or consisting of KLSSIESDV (SEQ ID NO: 5) or KLSSIETDV (SEQ ID NO: 43) linked to an internalization peptide. In some methods, the internalization peptide is a tat peptide. In some methods, the internalization peptide has an amino acid sequence comprising XGRKKRRQRRR (SEQ ID NO: 49), wherein X is an amino acid other than Y or nothing. In some methods, wherein X is F (SEQ ID NO:3). In some methods, the pharmacological agent has an amino acid sequence comprising FGYKKRRQRRRKLSSIESDV (SEQ ID NO:37) or FGYKKRRQRRRKLSSIETDV (SEQ ID NO: 68). In some methods, the pharmacological agent has an amino acid sequence consisting of FGYKKRRQRRRKLSSIESDV (SEQ ID NO:37) or FGYKKRRQRRRKLSSIETDV (SEQ ID NO: 68). In some methods, the pharmacological agent has an amino acid sequence comprising or consisting of YGRKKRRQRRRKLSSIESDV (SEQ ID NO: 26) or YGRKKRRQRRRKLSSIETDV (SEQ ID NO: 69). In some methods, the dose is 0.1-10 mg/kg. In some methods, a single dose is administered per episode of penetrative injury or risk thereof. In some methods, the administration is by intravenous infusion.

Some methods further comprise monitoring the subject for neurological deficits from the penetrative injury. In some methods, the monitoring determines cognitive functioning. In some methods, the monitoring determines pathology.

In any of the above methods, the temperature of the subject may be reduced responsive to the administering.

BRIEF DESCRIPTION OF THE DRAWINGS

FIGS. 1A-B show neuroscore after PBBI injury and treatment with Tat-NR2B9c (also known as NA1) or vehicle in two studies representing varying dosages.

FIG. 2A shows mean total footfaults per trial on a balance beam after PBBI injury and treatment with Tat-NR2B9c or vehicle.

FIG. 2B shows similar data to FIG. 2A except that mean footfaults per trial contralateral to site of injury only are shown.

FIG. 2C shows similar data to FIG. 2A except mean footfaults made per beam segment contralateral to site of injury are shown.

FIGS. 3A and B show two dose-response studies on a rotarod.

FIGS. 4A, B, C show dose response effects of Tat-NR2B9c (0.5 and 5.0 mg/kg only) on PBBI neuropathology in brain sections. FIG. 4A shows overall lesion volume, FIG. 4B right shows progression of lesion volume, and FIGS. 4B left and 4C show caudal sections.

FIGS. 5A-D show the effect of a single bolus injection of 20 mg/kg Tat-NR2B9c on neuroscore (A), rotarod (B) and Morris water maze tasks following PBBI (C and D).

FIGS. 6A-D show the effect of a multiple dosing regimes (at 0.5 mg/kg and 5 mg/kg) on neuroscore (A), rotarod (B) and Morris water maze tasks (D).

DEFINITIONS

A "chimeric peptide" means a peptide having two component peptides not naturally associated with one another joined to one another as a fusion protein or by chemical linkage.

A "fusion" protein or polypeptide refers to a composite polypeptide, i.e., a single contiguous amino acid sequence, made up of sequences from two (or more) distinct, heterologous polypeptides which are not normally fused together in a single polypeptide sequence.

The term "PDZ domain" refers to a modular protein domain of about 90 amino acids, characterized by significant sequence identity (e.g., at least 60%) to the brain synaptic protein PSD-95, the Drosophila septate junction protein Discs-Large (DLG), and the epithelial tight junction protein ZO1 (ZO1). PDZ domains are also known as Discs-Large homology repeats ("DHRs") and GLGF (SEQ ID NO:7) repeats. PDZ domains generally appear to maintain a core consensus sequence (Doyle, D. A., 1996, Cell 85: 1067-76). Exemplary PDZ domain-containing proteins and PDZ domain sequences disclosed in U.S. application Ser. No. 10/714,537, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 9, 10, 12, 14 or 16 residues), forms such a molecular complex. The molecular complex can be observed in vitro using the "A assay" or "G assay" described, e.g., in U.S. application Ser. No. 10/714,537, or in vivo.

The term "NMDA receptor," or "NMDAR," refers to a membrane associated protein that is known to interact with NMDA including the various subunit forms described below. Such receptors can be human or non-human (e.g., mouse, rat, rabbit, monkey).

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species. The term isolated or purified does not necessarily exclude the presence of other components intended to act in combination with an isolated species. For example, an internalization peptide can be described as isolated notwithstanding that it is linked to an active peptide.

A "peptidomimetic" refers to a synthetic chemical compound which has substantially the same structural and/or functional characteristics of a peptide consisting of natural amino acids. The peptidomimetic can contain entirely synthetic, non-natural analogues of amino acids, or can be a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. In a peptidomimetic of a chimeric peptide comprising an active peptide and an internalization peptide, either the active moiety or the internalization moiety or both can be a peptidomimetic.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Excitotoxicity is the pathological process by which neurons are damaged and killed by the overactivation of receptors for the excitatory neurotransmitter glutamate, such as the NMDA receptors, e.g., NMDAR 2B.

The term "subject" or "patient" includes humans and veterinary animals, such as mammals.

The term "agent" includes any compound including compounds with or without pharmaceutical activity, natural compounds, synthetic compounds, small molecules, peptides and peptidomimetics.

The term "pharmacologic agent" means an agent having a pharmacological activity. Pharmacological agents include compounds that are known drugs, compounds for which pharmacological activity has been identified but which are undergoing further therapeutic evaluation in animal models or clinical trials. A chimeric agent comprises a pharmacologic agent linked to an internalization peptide. An agent can be described as having pharmacological activity if it exhibits an activity in a screening system that indicates that the active agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

A tat peptide means a peptide comprising or consisting of GRKKRRQRRR (SEQ ID NO:1), in which no more than 5 residues are deleted, substituted or inserted within the sequence, which retains the capacity to facilitate uptake of a linked peptide or other agent into cells. Preferably any amino acid changes are conservative substitutions. Preferably, any substitutions, deletions or internal insertions in the aggregate leave the peptide with a net cationic charge, preferably similar to that of the above sequence. The amino acids of a tat peptide can be derivatized with biotin or similar molecule to reduce an inflammatory response.

Co-administration of a pharmacological agents linked to an internalization peptide and an anti-inflammatory agent means that the two agents are administered sufficiently proximately in time that the anti-inflammatory agent can inhibit an inflammatory response inducible by the internationalization peptide.

Statistically significant refers to a p-value that is <0.05, preferably <0.01 and most preferably <0.001.

An episode of penetrative injury or risk thereof means a period when signs and/or symptoms of the condition or risk are present interspersed by flanked by longer periods in which the signs and/or symptoms or risk are absent or present to a lesser extent.

A subject at risk of a disease or condition is a subject not presently having a disease or condition but who is at enhanced risk of developing the disease or condition by statistically significant or otherwise demonstrable measure, as further described below.

DETAILED DESCRIPTION OF THE INVENTION

I. General

The invention provides methods of treatment or prophylaxis of damaging effects of penetrative injury to the brain or other part of the central nervous system. The methods are based in part on results in a rodent model of penetrative ballistic injury showing that an inhibitor of PDF-95 NMDAR interaction is effective in inhibiting neurological deficits resulting from such injury. Such a model differs from the previously reported fluid percussion model in that the primary tissue damage from penetrative brain injury is extensive and might have been expected to overwhelm any effect of the treatment on secondary injury. The methods are useful for treating subjects having or at risk of penetrative brain injury, including subjects who have been shot in the head or at risk of such injury (e.g., military or law enforcement personnel).

II. Agents for Treating Disease

Although any agents can be screened for efficacy in the animal models or clinical trials described below, including agents that have failed previous clinical trials for stroke, a preferred class of agents inhibits interactions between PSD-95 and one or more NMDARs. Such agents are useful for reducing damaging effects of stroke and other neurological conditions mediated at least in part by NMDAR excitotoxicity. Such agents include peptides having an amino acid sequence including or based on the PL motif of a NMDA Receptor or PDZ domain of PSD95. Such peptides can also inhibit interactions between PSD-95 and nNOS and other glutamate receptors (e.g., kainite receptors or AMPA receptors), such as KV 1-4 and GluR6. Preferred peptides inhibit interaction between PDZ domains 1 and 2 of postsynaptic density-95 protein (PSD-95) (human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGHVYEKLSSIESDV (SEQ ID NO:11) and a PL motif ESDV (SEQ ID NO:12). Preferred peptides inhibit the human forms of PSD-95 and human NMDAR receptors. However, inhibition can also be shown from species variants of the proteins. A list of NMDA and glutamate receptors that can be used appears below:

TABLE 1

| | | | | | |
|---|---|---|---|---|---|
| | | NMDA Receptors With PL Sequences | | | |
| Name | GI or Acc# | C-terminal 20mer sequence | C-terminal 4mer sequence | internal PL? | PL ID |
| NMDAR1 | 307302 | HPTDITGPLNLSDPSVST VV (SEQ ID NO: 13) | STVV (SEQ ID NO: 27) | X | AA216 |
| NMDAR1-1 | 292282 | HPTDITGPLNLSDPSVST VV (SEQ ID NO: 13) | STVV (SEQ ID NO: 27) | X | AA216 |

TABLE 1-continued

NMDA Receptors With PL Sequences

| Name | GI or Acc# | C-terminal 20mer sequence | C-terminal 4mer sequence | internal PL? | PL ID |
|---|---|---|---|---|---|
| NMDAR1-4 | 472845 | HPTDITGPLNLSDPSVSTVV (SEQ ID NO: 13) | STVV (SEQ ID NO: 27) | X | AA216 |
| NMDAR1-3b | 2343286 | HPTDITGPLNLSDPSVSTVV (SEQ ID NO: 13) | STVV (SEQ ID NO: 27) | X | AA216 |
| NMDAR1-4b | 2343288 | HPTDITGPLNLSDPSVSTVV (SEQ ID NO: 13) | STVV (SEQ ID NO: 27) | X | AA216 |
| NMDAR1-2 | 11038634 | RRAIEREEGQLQLCSRHRES (SEQ ID NO: 14) | HRES (SEQ ID NO: 28) | | |
| NMDAR1-3 | 11038636 | RRAIEREEGQLQLCSRHRES (SEQ ID NO: 14) | HRES (SEQ ID NO: 28) | | |
| NMDAR2C | 6006004 | TQGFPGPCTWRRISSLESEV (SEQ ID NO: 15) | ESEV (SEQ ID NO: 29) | X | AA180 |
| NMDAR3 | 560546 | FNGSSNGHVYEKLSSIESDV (SEQ ID NO: 11) | ESDV (SEQ ID NO: 12) | X | AA34.1 |
| NMDAR3A | 17530176 | AVSRKTELEEYQRTSRTCES (SEQ ID NO: 16) | TCES (SEQ ID NO: 30) | | |
| NMDAR2B | 4099612 | FNGSSNGHVYEKLSSIESDV (SEQ ID NO: 11) | ESDV (SEQ ID NO: 12) | X | |
| NMDAR2A | 558748 | LNSCSNRRVYKKMPSIESDV (SEQ ID NO: 17) | ESDV (SEQ ID NO: 12) | X | AA34.2 |
| NMDAR2D | 4504130 | GGDLGTRRGSAHFSSLESEV (SEQ ID NO: 18) | ESEV (SEQ ID NO: 29) | X | |
| Glutamate receptor delta 2 | AF009014 | QPTPTLGLNLGNDPDRGTSI (SEQ ID NO: 19) | GTSI (SEQ ID NO: 31) | X | |
| Glutamate receptor 1 | I28953 | MQSIPCMSHSSGMPLGATGL (SEQ ID NO: 20) | ATGL (SEQ ID NO: 32) | X | |
| Glutamate receptor 2 | L20814 | QNFATYKEGYNVYGIESVKI (SEQ ID NO: 21) | SVKI (SEQ ID NO: 33) | X | |
| Glutamate receptor 3 | AF167332 | QNYATYREGYNVYGTESVKI (SEQ ID NO: 22) | SVKI (SEQ ID NO: 33) | X | |
| Glutamate receptor 4 | U16129 | HTGTAIRQSSGLAVIASDLP (SEQ ID NO: 23) | SDLP (SEQ ID NO: 34) | X | |
| Glutamate receptor 5 | U16125 | SFTSILTCHQRRTQRKETVA (SEQ ID NO: 24) | ETVA (SEQ ID NO: 35) | X | |
| Glutamate receptor 6 | U16126 | EVINMHTFNDRRLPGKETMA (SEQ ID NO: 25) | ETMA (SEQ ID NO: 36) | X | |

Some peptides inhibit interactions between PSD-95 and multiple NMDAR subunits. In such instances, use of the peptide does not necessarily require an understanding of the respective contributions of the different NMDARs to excitatory neurotransmission. Other peptides are specific for a single NMDAR.

Peptides can include or be based on a PL motif from the C-terminus of any of the above subunits and have an amino acid sequence comprising [S/T]-X-[V/L]. This sequence preferably occurs at the C-terminus of the peptides of the invention. Preferred peptides have an amino acid sequence comprising [E/D/N/Q]-[S/T]-[D/E/Q/N]-[v/l] (SEQ ID NO:38) at their C-terminus Exemplary peptides comprise: ESDV (SEQ ID NO:12), ESEV (SEQ ID NO:29), ETDV (SEQ ID NO:39), ETEV (SEQ ID NO:40), DTDV (SEQ ID NO:41), and DTEV (SEQ ID NO:42) as the C-terminal amino acids. Two particularly preferred peptides are KLSSIESDV (SEQ ID NO:5), and KLSSIETDV (SEQ ID NO:43). Such peptides usually have 3-25 amino acids (without an internalization peptide), peptide lengths of 5-10 amino acids, and particularly 9 amino acids (also without an internalization peptide) are preferred. In some such peptides, all amino acids are from the C-terminus of an NMDA receptor (not including amino acids from an internalization peptide).

Other peptides that inhibit interactions between PDS95 and NDMARs include peptides from PDZ domain 1 and/or 2 of PSD-95 or a subfragment of any of these that inhibits interactions between PSD-95 and an NMDA receptor, such as NMDA 2B. Such active peptides comprise at least 50, 60, 70, 80 or 90 amino acids from PDZ domain 1 and/or PDZ domain 2 of PSD-95, which occur within approximately amino acids 65-248 of PSD-95 provided by Stathakism, Genomics 44(1):71-82 (1997) (human sequence) or NP_031890.1, GI:6681195 (mouse sequence) or corresponding regions of other species variants.

Peptides and peptidomimetics of the invention can contain modified amino acid residues for example, residues that are N-alkylated. N-terminal alkyl modifications can include e.g., N-Methyl, N-Ethyl, N-Propyl, N-Butyl, N-Cyclohexylmethyl, N-Cyclyhexylethyl, N-Benzyl, N-Phenylethyl, N-phenylpropyl, N-(3, 4-Dichlorophenyl)propyl, N-(3,4-Difluorophenyl)propyl, and N-(Naphthalene-2-yl)ethyl).

Bach, J. Med. Chem. 51, 6450-6459 (2008) and WO 2010/004003 has described a series of analogs of NR2B9c. PDZ-binding activity is exhibited by peptides having only three C-terminal amino acids (SDV). Bach also reports analogs having an amino acid sequence comprising or consisting of $X_1X_3X_2V$ (SEQ ID NO:8), wherein $X_1$ is selected from among E, Q, and A, or an analogue thereof, $X_2$ is selected from among A, Q, D, N, N-Me-A, N-Me-Q, N-Me-D, and N-Me-N or an analogue thereof and $X_3$ is selected from alternative amino acids t or S. Optionally the peptide is N-alkylated in position P3 position (third amino acid from C-terminus). The peptide can be N-alkylated with a cyclohexane or aromatic substituent, and further comprises a spacer group between the substituent and the terminal amino group of the peptide or peptide analogue, wherein the spacer is an alkyl group, preferably selected from among methylene, ethylene, propylene and butylene. The aromatic substituent can be a naphthalen-2-yl moiety or an aromatic ring substituted with one or two halogen and/or alkyl group.

Other modifications can also be incorporated without adversely affecting the activity and these include substitution of one or more of the amino acids in the natural L-isomeric form with amino acids in the D-isomeric form. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form. Thus, a peptidomimetic may include 1, 2, 3, 4, 5, at least 50%, or all D-amino acid resides. A peptidomimetic containing some or all D residues is sometimes referred to an "inverso" peptide.

Peptidomimetics also include retro peptides. A retro peptide has a reverse amino acid sequence. Peptidomimetics also include retro inverso peptides in which the order of amino acids is reversed from so the originally C-terminal amino acid appears at the N-terminus and D-amino acids are used in place of L-amino acids. WO 2008/014917 describes a retro-inverso analog of Tat-NR2B9c having the amino acid sequence vdseissllurrqrrkkrgyin (SEQ ID NO: 4) of which the first nine amino acids correspond to NR2B9c and the remainder to tat, (lower case letters indicating D amino acids), and reports it to be effective inhibiting cerebral ischemia. Another effective peptide described herein is RvTat-NR2B9c (RRRQRRKKRGYKLSSIESDV SEQ ID NO:6)

A linker, e.g., a polyethylene glycol linker, can be used to dimerize the active moiety of the peptide or the peptidomimetic to enhance its affinity and selectivity towards proteins containing tandem PDZ domains. See e.g., Bach et al., (2009) Angew. Chem. Int. Ed. 48:9685-9689 and WO 2010/004003. A PL motif-containing peptide is preferably dimerized via joining the N-termini of two such molecules, leaving the C-termini free. Bach further reports that a pentamer peptide IESDV (SEQ ID NO:9) from the C-terminus of NMDAR 2B was effective in inhibiting binding of NMDAR 2B to PSD95. Optionally, about 2-10 copies of ethylene glycol monomer are joined in tandem as a PEG linker.

Appropriate pharmacological activity of peptides, peptidomimetics or other agent can be confirmed if desired, using previously described rat models of stroke before testing in the rodent and clinical trials described in the present application. Peptides or peptidomimetics can also be screened for capacity to inhibit interactions between PSD-95 and NMDAR 2B using assays described in e.g., US 20050059597, which is incorporated by reference. Useful peptides typically have IC50 values of less than 50 μM, 25 μM, 10 μM, 0.1 μM or 0.01 μM in such an assay. Preferred peptides typically have an IC50 value of between 0.001-1 μM, and more preferably 0.05-0.5 or 0.05 to 0.1 μM. When a peptide or other agent is characterized as inhibiting binding of one interaction, e.g., PSD-95 interaction to NMDAR 2B, such description does not exclude that the peptide or agent also inhibits another interaction, for example, inhibition of PSD-95 binding to nNOS.

Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Pharmacological agents also include small molecules that inhibit interactions between PSD95 and NMDAR 2B, and/or other interactions described above. Suitable small-molecule inhibitors are described in WO/2009/006611. An exemplary class of suitable compounds are of the formula:

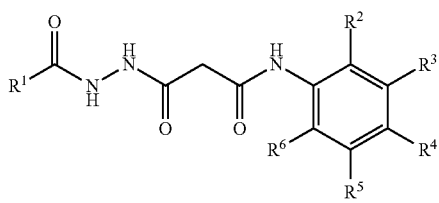

wherein $R^1$ is a member selected from the group consisting of cyclohexyl substituted with 0-4 $R^7$, phenyl substituted with 0-4 $R^7$, —$(CH_2)_u$—$(CHR^8R^9)$, a branched $C_{1-6}$ alkyl (isopropyl, isobutyl, 1-isopropyl-2-methyl-butyl, 1 ethyl-propyl), and —NH—C(O)—$(CR^{10}R^{11})_v$H;

each $R^7$ is independently a member selected from the group consisting of $C_{1-6}$ alkyl, $C_{1-6}$ alkoxy, —$C(O)R^{12}$, OH, COOH, —NO, N-substituted indoline and a cell membrane translocation peptide;

each $R^8$ and $R^9$ is independently selected from the group consisting of H, OH, cyclohexane, cyclopentane, phenyl, substituted phenyl and cyclopentadiene;

each $R^{10}$ and $R^{11}$ is independently selected from the group consisting of H, cyclohexane, phenyl and a cell membrane translocation peptide;

$R^{12}$ is a member selected from the group consisting of $C_{1-6}$ alkyl and aryl; and each of u and v are independently from 0 to 20;

wherein one of $R^2$, $R^3$, $R^4$, $R^5$ and $R^6$ is —COOH, and wherein the remainder of $R^2$, $R^3$, $R^4$, $R^5$ and $R^6$ are each independently selected from the group consisting of F, H, $OCH_3$ and $CH_3$.

One such compound is 0620-0057, the structure of which is:

0620-0057

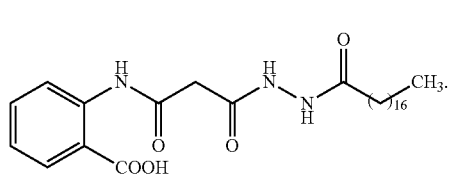

A pharmacological agent can be linked to an internalization peptide to facilitate uptake into cells and/or across the blood brain barrier. Internalization peptides, also known as cell membrane transduction peptides or cell penetrating peptides, are a well-known class of relatively short (e.g., 8-30 amino acids) peptides that allow many cellular or viral proteins to traverse membranes. Such peptides typically have a cationic charge from an above normal representation (relative to proteins in general) of arginine and/or lysine residues that is believed to facilitate their passage across membranes. Some such peptides have at least 5, 6, 7 or 8 arginine and/or lysine residues. Examples include the antennapedia protein (Bonfanti, Cancer Res. 57, 1442-6 (1997)) (and variants thereof), the tat protein of human immunodeficiency virus, the protein VP22, the product of the UL49 gene of herpes simplex virus type 1, Penetratin, SynB1 and 3, Transportan, Amphipathic, gp41NLS, polyArg, and several plant and bacterial protein toxins, such as ricin, abrin, modeccin, diphtheria toxin, cholera toxin, anthrax toxin, heat labile toxins, and Pseudomonas aeruginosa exotoxin A (ETA). Other examples are described in the following references (Temsamani, Drug Discovery Today, 9(23):1012-

1019, 2004; De Coupade, Biochem J., 390:407-418, 2005; Saalik Bioconjugate Chem. 15: 1246-1253, 2004; Zhao, Medicinal Research Reviews 24(1):1-12, 2004; Deshayes, Cellular and Molecular Life Sciences 62:1839-49, 2005) (all incorporated by reference).

A preferred internalization peptide is tat from the HIV virus. A tat peptide reported in previous work comprises or consists of the standard amino acid sequence YGRKKRRQRRR (SEQ ID NO:2) found in HIV Tat protein. Thus two preferred agents incorporating this tat peptide are the peptides comprising or consisting of the amino acid sequence YGRKKRRQRRRKLSSIESDV, SEQ ID NO:26 (also known as Tat-NR2B9c or NA1) or YGRKKRRQRRRKLSSIETDV (SEQ ID NO:69). If additional residues flanking such a tat motif are present (beside the pharmacological agent) the residues can be for example natural amino acids flanking this segment from a tat protein, spacer or linker amino acids of a kind typically used to join two peptide domains, e.g., gly (ser)4 (SEQ ID NO:44), TGEKP (SEQ ID NO:45), GGRRGGGS (SEQ ID NO:46), or LRQRDGERP (SEQ ID NO:47) (see, e.g., Tang et al. (1996), J. Biol. Chem. 271, 15682-15686; Hennecke et al. (1998), Protein Eng. 11, 405-410)), or can be any other amino acids that do not significantly reduce capacity to confer uptake of the variant without the flanking residues. Preferably, the number of flanking amino acids other than an active peptide does not exceed ten on either side of YGRKKRRQRRR (SEQ ID NO:2). One suitable tat peptide comprising additional amino acid residues flanking the C-terminus of YGRKKRRQRRR (SEQ ID NO:2) is YGRKKRRQRRRPQ (SEQ ID NO:48). However, preferably, no flanking amino acids are present.

Variants of the above tat peptide having reduced capacity to bind to N-type calcium channels are described by WO/2008/109010. Such variants can comprise or consist of an amino acid sequence XGRKKRRQRRR (SEQ ID NO:49), in which X is an amino acid other than Y or nothing (in which case G is a free N-terminal residue). A preferred tat peptide has the N-terminal Y residue substituted with F. Thus, a tat peptide comprising or consisting of FGRKKRRQRRR (SEQ ID NO:3) is preferred. Another preferred variant tat peptide consists of GRKKRRQRRR (SEQ ID NO:1). Other tat derived peptides that facilitate uptake of a pharmacological agent without inhibiting N-type calcium channels include those presented in Table 2 below.

TABLE 2

| | |
|---|---|
| X-FGRKKRRQRRR (F-Tat) (residues 2-12 of this sequence are encompassed in SEQ ID NO: 3; full-length sequence disclosed as SEQ ID NO: 10) | |
| X-GKKKKKQKKK | (SEQ ID NO: 50) |
| X-RKKRRQRRR | (SEQ ID NO: 51) |
| X-GAKKRRQRRR | (SEQ ID NO: 52) |
| X-AKKRRQRRR | (SEQ ID NO: 53) |
| X-GRKARRQRRR | (SEQ ID NO: 54) |
| X-RKARRQRRR | (SEQ ID NO: 55) |
| X-GRKKARQRRR | (SEQ ID NO: 56) |
| X-RKKARQRRR | (SEQ ID NO: 57) |

TABLE 2-continued

| | |
|---|---|
| X-GRKKRRQARR | (SEQ ID NO: 58) |
| X-RKKRRQARR | (SEQ ID NO: 59) |
| X-GRKKRRQRAR | (SEQ ID NO: 60) |
| X-RKKRRQRAR | (SEQ ID NO: 61) |
| X-RRPRRPRRPRR | (SEQ ID NO: 62) |
| X-RRARRARRARR | (SEQ ID NO: 63) |
| X-RRRARRRARR | (SEQ ID NO: 64) |
| X-RRRPRRRPRR | (SEQ ID NO: 65) |
| X-RRPRRPRR | (SEQ ID NO: 66) |
| X-RRARRARR | (SEQ ID NO: 67) |

X can represent a free amino terminus, one or more amino acids, or a conjugated moiety. Internalization peptides can be used in inverso or retro or inverso retro form with or without the linked peptide or peptidomimetic being in such form. For example, a preferred chimeric peptide has an amino acid sequence comprising or consisting of RRRQR-RKKRGYKLSSIESDV (SEQ ID NO:7).

Internalization peptides can be attached to pharmacological agents by conventional methods. For example, the agents can be joined to internalization peptides by chemical linkage, for instance via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyl-dithio) propionate (SPDP) or N,N'-(1,3-phenylene) bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m, m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

For pharmacological agents that are peptides attachment to an internalization peptide can be achieved by generating a fusion protein comprising the peptide sequence fused, preferably at its N-terminus, to an internalization peptide.

Pharmacologic peptides, optionally fused to tat peptides, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

III. Patients Amenable To Treatment

The methods are suitable for treatment on subjects having penetrative injury of the brain or other component of the CNS. A penetrative injury is one resulting from the displacement or destruction of CNS tissue by a solid object passing from outside the body into and/or through the CNS (e.g., through the skull), and would not include for example, a fluid percussion injury in which injury in effected by pressure from an injected fluid. In a penetrative injury, the solid object may transiently pass through the brain leaving damage in its path or may become embedded until or unless removed by a surgical procedure. Penetrative injuries can be, for example, the result of warfare, other combat, law enforcement, criminal activity and other violent situations, in which more primary tissue damage is present than a fluid percussion injury or an injury incidental to surgery. The injury can be the result of a gunshot wound, solid matter released by an explosion, such as a bomb, or a sharp object, such as a knife, spear, blade, or impalement. Such injury can be to the brain or spinal cord. Such patients are preferably treated as soon as possible, and in any event within a window of 24, 12, 6, 3 or 1 hour after penetrative injury has occurred.

Patients treated by the present methods can also be subject to surgery for primary tissue damage resulting from a penetrative injury to the CNS (e.g., remove a bullet, stop bleeding, repair a nerve). In such case, the treatment can also be useful in reducing damaging secondary effects from the surgery itself (e.g., infarction) as well as secondary effects from the penetrative injury. However, the primary damage from the penetrative injury is usually greater than the any incidental damage resulting from surgery, so in such situations, the present methods are primarily for treatment of the secondary damage resulting from penetrative injury. Although damage to the CNS resulting solely from therapeutic or diagnostic surgery can also be treated with the pharmacological agents disclosed in the present application (see U.S. Ser. No. 61/185,989 filed Jun. 10, 2009, published as WO2010/144721), injuries resulting solely incidental to therapeutic or diagnostic surgery are not considered penetrative injuries as defined herein.

The methods are also suitable for treatment of subjects at enhanced risk of such injury. Such subjects include military personnel about to enter a battlefield or other place of anticipated combat or law enforcement personnel whose duties place them in proximity with armed criminal activities. Such individuals are preferably treated at or as close as possible to the time of being placed at risk of penetrative injury (e.g., before entering a battlefield or confronting armed criminals) and in any event within a window of less than 24, 12, 6, 3 or 1 hour before such occurrence.

Patients amenable to treatment may or may not have and/or be at enhanced risk of other diseases or disorders for which treatment with PSD-95 antagonists has previously been proposed (i.e., co-morbid diseases amenable to treatment with a PSD-95 antagonist). These diseases and conditions include excitotoxicity mediated diseases, stroke, epilepsy, hypoxia, traumatic injury to the CNS not associated with stroke such as traumatic brain injury and spinal cord injury, Alzheimer's disease and Parkinson's disease. A stroke is a rapidly developing injury to the CNS due to disturbance of blood supply to an area of the CNS. Co-morbidity with stroke thus means contemporaneous with such developing injury. In patients, in whom such a comorbid disease is present, the agents of the invention can be effective against penetrative injury and the co-morbid disease.

IV. Methods of Treatment

A pharmacological agents optionally linked to an internalization peptide is administered in an amount, frequency and route of administration effective to cure or reduce, or inhibit further deterioration of at least one sign or symptom of penetrative brain injury. Unless otherwise indicated dosages for a pharmacologic agent linked to an internalization peptide refer to the whole agent rather than just the pharmacological agent component of the chimeric agent. A therapeutically effective amount means an amount of a pharmacological agent (including internalization peptide) if present sufficient to cure or reduce or inhibit further deterioration of at least one sign or symptom of penetrative brain injury in a population of patients (or animal models) suffering from the disease treated with an agent of the invention relative to the damage in a control population of patients (or animal models) suffering from that disease or condition who are not treated with the agent. The amount is also considered therapeutically effective if an individual treated patient achieves an outcome more favorable than the mean outcome in a control population of comparable patients not treated by methods of the invention. A therapeutically effective regime involves the administration of a therapeutically effective dose at a frequency and route of administration needed to achieve the intended purpose. A single dose of agent is often sufficient for treatment of a penetrative brain injury. Multiple dosing regimes are also effective.

The invention also provides methods and compositions for the prophylaxis of penetrative injury to the brain or other CNS component. Usually such a subject has an increased likelihood of developing such an injury (e.g., military, law enforcement personnel) relative to a control population. The control population for instance can comprise one or more individuals selected at random from the general population (e.g., matched by age, gender, race and/or ethnicity). A subject can be considered at risk for a disorder if a "risk factor" associated with that disorder is found to be associated with that subject. A risk factor can include any activity, trait, event or property associated with a given disorder, for example, through statistical or epidemiological studies on a population of subjects. A subject can thus be classified as being at risk for a disorder even if studies identifying the underlying risk factors did not include the subject specifically.

A pharmacological agent optionally linked to an internalization peptide is administered to a patient at risk of penetrative injury to the brain or other component of the CNS in an amount, frequency and route sufficient to prevent, delay or inhibit development of at least one sign or symptom of penetrative injury to the brain or other component of the CNS. A prophylactically effective amount means an amount of pharmacological agent sufficient significantly to prevent, inhibit or delay at least one sign or symptom of such penetrative injury in a population of patients (or animal models) at risk of the injury treated with the agent compared to a control population of patients (or animal models) at risk of the injury not treated with a chimeric agent of the invention. The amount is also considered prophylactically effective if an individual treated patient achieves an outcome more favorable than the mean outcome in a control population of comparable patients not treated by methods of the invention. A prophylactically effective regime involves the administration of a prophylactically effective dose at a frequency and route of administration needed to achieve the intended purpose. For prophylaxis of damaging effects of penetrative injury to the brain or other component of the CNS, a single dose of agent per episode of risk is usually sufficient.

Depending on the agent, administration can be parenteral, intravenous, nasal, oral, subcutaneous, intra-arterial, intracranial, intrathecal, intraperitoneal, topical, intranasal or intramuscular. Intravenous administration is preferred for peptide agents.

For chimeric agents including an internalization peptide, particularly a HIV tat peptide comprising the amino acid sequence, the agent may or may not be co-administered with an anti-inflammatory agent to reduce release or histamine and its downstream effects associated with high levels of the internalization peptide. Preferred agents for co-administration are inhibitors of mast cell degranulation, such as cromolyn. Anti-histamines or corticosteroids can also be used, particularly in combinations or higher dosages (see WO/2009/076105 and U.S. Ser. No. 61/185,943, filed Jun. 10, 2009, published as WO 2010/144742).

For administration to humans, a preferred dose of the chimeric agent Tat-NR2B9c can be, for example, from 0.1-20 mg/kg, 0.1-10 mg/kg or 0.5-3 mg/kg, 1-3 mg/kg, 2-3 mg/kg, 0.5-2 mg/kg or 2.7 mg/kg. Indicated dosages should be understood as including the margin of error inherent in the accuracy with which dosages can be measured in a typical hospital setting. Doses in rats can be converted to dosages in humans by dividing by a correction factor of 6.2 that accounts for the different surface areas of the species. However, doses in rats can also be used in humans without such a correction factor. Because the extremely acute nature of penetrative injuries to the brain and other components of the CNS may leave very little room for a second administration should the first administration prove inadequate or insufficient, a dose approaching the maximum tolerated dose is preferred in some patients.

The dosages indicated above are for the chimeric agent Tat-NR2B9c (YGRKKRRQRRRKLSSIESDV, SEQ ID NO:26). Equivalent dosages for other agents to achieve the same effect can be determined by several approaches. For close variants of that agent in which one or a few amino acids are substituted, inserted or deleted and the molecular weight remains the same within about +/− 25%, the above dosages are still a good guide. However, in general, for other agents, equivalent dosages can vary depending on the molecular weight of the agent with and without internalization peptide if present, its Kd for its target, and its pharmacokinetic and pharmacodynamic parameters. For some agents, equivalent dosages can be calculated so as to deliver an equimolar amount of the pharmacological agent. For other agent, further adjustment is made to account for differences in Kd or pharmacokinetic or pharmacodynamic parameters. For some agents, equivalent dosages are determined empirically from the dose achieved to reach the same endpoint in an animal model or a clinical trial.

Peptide agents, such as Tat-NR2B9c are preferably delivered by infusion into a blood vessel, more preferably by intravenous infusion. The time of the infusion can affect both side effects (due e.g., to mast cell degranulation and histamine release) and efficacy. In general, for a given dosage level, a shorter infusion time is more likely to lead to histamine release. However, a shorter infusion time also may result in improved efficacy. Although practice of the invention is not dependent on an understanding of mechanism, the latter result can be explained both because of the delay being significant relative to development of pathology in the patient and because of the delay being significant relative to the plasma half-life of the chimeric agent, as a result of which the chimeric agent does not reach an optimal therapeutic level. For the chimeric agent Tat-NR2B9c, a preferred infusion time providing a balance between these considerations is 5-15 minutes and more preferably 10 min. Indicated times should be understand as including a margin of error of +/−10%. Infusion times do not include any extra time for a wash out diffusion to wash out any remaining droplets from an initial diffusion that has otherwise proceeded to completion. The infusion times for Tat-NR2B9c can also serve as a guide for other pharmacological agents, optionally linked to internalization peptides, particularly close variants of Tat-NR2B9c, as discussed above.

VII. Pharmaceutical Compositions

The chimeric or other agents of the invention can be administered in the form of a pharmaceutical composition. Pharmaceutical compositions are typically manufactured under GMP conditions. Pharmaceutical compositions for parenteral administration are preferentially sterile (e.g., filter sterilization of peptide) and free of pyrogens. Pharmaceutical compositions can be provided in unit dosage form (i.e., the dosage for a single administration). Pharmaceutical compositions can be formulated in conventional manner using one or more physiologically acceptable carriers, diluents, excipients or auxiliaries that facilitate processing of chimeric agents into preparations which can be used pharmaceutically. Proper formulation is dependent on the route of administration chosen.

An exemplary formulation of the chimeric agent Tat-NR2B9c contains the peptide in normal saline (0.8-1.0% and preferably 0.9% saline) at a concentration of 10-30 mg/ml, for example 18-20 mg/ml. When stored frozen, such a composition is stable (insignificant degradation or aggregation of the peptide) for a period of two or more years. Although additional excipients can be added, normal saline without such excipients is sufficient to obtain this stability. For use such a composition is thawed and diluted into a larger volume of normal saline for infusion into a blood vessel. Another composition can be made by lyophilizing the chimeric agent Tat-NR2B9c at a concentration of 1-50 mg/ml in normal saline in the presence or absence of excipients. Such excipients can include those to increase stability or inhibit bacterial, viral or other pathogen growth that could degrade the drug. The lyophilized composition is stable at −20° C. or at room temperature. The lyophilized composition can be reconstituted in normal saline (i.e., reconstituted so as to provide Tat-NR2B in normal saline).

EXAMPLES

1. Rat Model of Penetrative Brain Injury

Male Sprague-Dawley rats (250-300 g) were subjected to a simulated ballistic wound to the right frontal hemisphere implemented by an inflatable penetrating probe. Three levels of injury severity were compared to control animals. Neurological and physiological outcome was assessed over a 3-day recovery period and brain tissue collected at 72 h for histopathological evaluation. Brain-injured regions included the ipsilateral frontal cortex and striatum with volumetric increases in intracranial hemorrhage (5-18 mm3) and lesion size (9-86 mm3) related to severity. Similarly, hemispheric swelling increased (3-14%) following PBI, associated with a significant rise in intracranial pressure. Astrogliosis was present in regions adjacent to the core-injury along with microglial and leukocyte infiltration. Injury remote to the lesion was observed in the cerebral peduncle that may have accounted, in part, for observed neurological deficits. Neurological and balance beam testing revealed sensorimotor deficits that persisted through 72 h. Severe electroencephalographic disturbances included the occurrence of cortical spreading depression, slow-waves, and brain seizure activity. In conclusion, this rat PBI model replicates diverse, salient features of clinical PBI pathology, generates reproducible and quantifiable measures of outcome, and is scalable by injury severity, rendering it an attractive vehicle for experimental brain trauma research. The model is further described by Williams et al., *J. Neurotrauma* 22, 313-331 (2005).

2. Treatment of Penetrative Injury

Tat-NR2B9c was administered i.v. in the jugular vein by an 8 minute infusion 30 minutes after inducing brain injury. Rats were sacrificed for histologic examination after 7 days. The dose of Tat-NR2B9c was Study I: 0.5 and 5.0 mg/ml/kg and Study II: 0.05, 0.275, and 0.5 mg/ml/kg. The rats were subject to the following treatments in Study I and II (sham=rat not subject to ballistic injury, PBBI=penetrative ballistic brain injury, veh=vehicle).

Study 1
SHAM/veh (n=10)
PBBI/veh (n=10)
PBBI, Tat-NR2B9c 0.5 mg/kg (n=10)
PBBI Tat-NR2B9c 5.0 mg/kg (n=10)

Study 2
SHAM/veh (n=10)
PBBI/veh (n=10)
Tat-NR2B9c 0.05 mg/kg (n=10)
Tat-NR2B9c 0.275 mg/kg (n=10)
Tat-NR2B9c 0.50 mg/kg (n=10)

Body weight was assessed at time 0 (baseline), 24, 72 h and 7 days post injury. Body temperature was assessed at time 0, 30 min (prior to treatment), 2, 24, 72 h, and 7 days post injury. Neuroscore was assessed at 0, 30 min (prior to treatment), 24, 72 h, 7 days post injury. Balance beam was assessed at time 0, 3, and 7 days post injury. Rotarod was assessed at time 0 and 7 days post injury.

Study 1 evaluated two concentrations of Tat-NR2B9c (0.5 mg/kg and 5.0 mg/kg) (n=10 each group) with a survival period of 1 week. Based on the results of Study 1, Study 2 evaluated two lower concentrations of Tat-NR2B9c (0.05 and 0.275 mg/kg) and repeated the 0.5 mg/kg dose from Study 1. Behavioral and histological endpoints for both experiments included neurological assessments on neuroscore, balance beam, and rotarod tests, and lesion reconstruction on H&E stained sections. All PBBI rats showed significant neurological impairment out to 7 days post-injury.

FIGS. 1A and B shows neuroscore in Studies 1 and 2. In Study 1, the 0.5 mg/kg dose of Tat-NR2B9c produced a significant, reduction in PBBI-induced neurological deficits at 72 hours post-PBBI. In Study 2, the 0.5 mg/kg dose of Tat-NR2B9c proved to be the most effective in reducing injury-induced neurological deficits at both 3 and 7 days post PBBI. Columns=means; error bars=SEM; *$p<0.05$ compared to PBBI; †$p<0.05$ compared to 0.05 mg/kg Tat-NR2B9c; #$p<0.05$ compared to 0.275 mg/kg Tat-NR2B9c.

FIG. 2A shows mean total footfaults per trial on a balance beam (contra- and ipsilateral combined) averaged from 3 consecutive trials. A maximal total footfault score of 18 (12 contralateral; 6 ipsilateral) was assigned when animals were unable to cross the beam. The upper portion of FIG. 2A includes a total of 7 rats (three PBBI, two low-dose Tat-NR2B9c, and two high-dose Tat-NR2B9c of 10 animals per group) unable to cross the beam at 3 days post-PBBI that were assigned maximal footfault scores. At 7 days post-PBBI, with the exception of one high-dose Tat-NR2B9c animal, all rats were able to cross the beam. The lower portion of FIG. 2A includes a total of 8 rats (three PBBI, three low-dose Tat-NR2B9c, one medium-dose Tat-NR2B9c, and one high-dose Tat-NR2B9c of 10-11 animals per group) unable to cross the beam at 3 days post-PBBI that were assigned maximal footfault scores. At 7 days post-PBBI, with the exception of one PBBI and one low-dose Tat-NR2B9c, all rats were able to cross the beam. *p<0.05 compared to PBBI; †p<0.05 compared to 0.50 mg/kg Tat-NR2B9c.

FIG. 2B shows mean footfaults per trial (contralateral to site of injury only) averaged from 3 consecutive trials. A maximal total footfault score of 12 was assigned when animals were unable to cross the beam. The upper portion of FIG. 2B from Study 1 includes a total of 7 rats (three PBBI, two low-dose Tat-NR2B9c, and two high-dose Tat-NR2B9c) unable to cross the beam at 3 days post-PBBI that were assigned maximal footfault scores. At 7 days post-PBBI, with the exception of one high-dose Tat-NR2B9c animal, all rats were able to cross the beam. The lower portion of the figure from Study 2 includes a total of 8 rats (three PBBI, three low-dose Tat-NR2B9c, one medium-dose Tat-NR2B9c, and one high-dose Tat-NR2B9c) unable to cross the beam at 3 days post-PBBI that were assigned maximal footfault scores. At 7 days post-PBBI, with the exception of one PBBI and one low-dose Tat-NR2B9c, all rats were able to cross the beam. *p<0.05 compared to PBBI.

FIG. 2C shows mean footfaults made per beam segment contralateral to site of injury. For both dose-response studies, rats were trained to criteria on the tapered balance beam prior to PBBI and tested at 3 and 7 days post-PBBI (3 trials each time point). Following PBBI, all injured groups showed significant motor abnormalities on the balance beam task at both time points tested, with foot faults increasing in frequency as the beam narrowed in width (S1-S3=widest-narrowest beam segment). The upper portion of FIG. 2C based on Study 1 shows 3 days post-PBBI, animals treated with the 0.5 and 5.0 mg/kg doses of Tat-NR2B9c made significantly fewer foot faults than the PBBI rats, particularly on the narrowest segment of the beam (S3). The lower portion of FIG. 2C from Study 2 shows 3 days post-PBBI, animals treated with 0.275 and 0.50 mg/kg made fewer footfaults than the PBBI animals on the narrowest segment of the beam. Columns=means; error bars=SEM; *p<0.05 compared to PBBI.

FIGS. 3A and B show dose-response studies on a rotarod. Rats were trained to criteria on the fixed-speed version of the rotarod task prior to PBBI and tested at 7 days post-PBBI. FIG. 3A shows from Study 1 that the 0.50 mg/kg dose of Tat-NR2B9c promoted significant recovery (to SHAM levels) at the two lower speeds (10-15 rpm) but not at higher speeds (20-25 rpm) on the rotarod task. FIG. 3B shows from Study 2 the 0.50 mg/kg dose of Tat-NR2B9c was more effective than the lower doses at reducing PBBI-induced motor abnormalities on the rotarod task. Columns=means; error bars=SEM; *p<0.05 compared to PBBI FIGS. 4A, B, C show dose response effects of Tat-NR2B9c (0.5 and 5.0 mg/kg only) on PBBI neuropathology. Post-injury administration of Tat-NR2B9c (either dose) did not significantly reduce overall lesion volume (A, B right panel). However there was a trend, particularly in the more caudal sections (B left panel, C) providing evidence that Tat-NR2B9c (both doses) reduced the extent (i.e., volume) of the lesion. Columns/data points=means; error bars=SEM; *p<0.05 Tat-NR2B9c (NA1) 0.5 mg compared to PBBI; †p<0.05 tat-NR2B9c (NA1) 5.0 mg compared to PBBI.

FIGS. 5A-5D show the effects of treating PBBI animals with a higher dose of Tat-NR2B9c (20 mg/kg). As with the previous experiments, Tat-NR2B9c was administered as a slow bolus (8 minute) 30 minutes after PBBI. FIG. 5A shows that animals treated with Tat-NR2B9c showed a consistent improvement in neuroscore, even after 7 days. FIG. 5B shows that animals treated with Tat-NR2B9c showed significantly improved performance on rotarod tasks, especially at lower speeds. Mean rotarod latencies across speeds were >2-fold higher in the tat-NR2B9c (NA1) (20 mg/kg) group relative to vehicle-treated PBBI rats (means: PBBI/veh=13±3s; *Tat-NR2B9c (NA1) 20 mg/kg=29±3s; *p<0.05). Both Tat-NR2B9c and vehicle-treated PBBI rats showed similar learning curves during the acquisition phase of the Morris Water Maze (MWM) task. However, Tat-NR2B9c (20 mg/kg) resulted in a 2-fold improvement in memory retention in the probe trial, measured by % time spent exploring the missing platform zone (FIGS. 5C and 5D; means: PBBI/veh=15±2%; *Tat-NR2B9c 20 mg/kg=29±4%; *p<0.05) Treatment with Tat-NR2B9c (20 mg/kg) also resulted in a significant (33%) reduction in total lesion volume by TTC staining (means: PBBI/veh=56±7 mm$^3$; *Tat-NR2B9c (NA1(_20 mg/kg=37±4 mm$^3$; *p<0.05).

FIGS. 6A-D show the effects of multiple dosing regimes on neuroscore, rotarod and MWM performance Animals were given four injections of Tat-NR2B9c post-PBBI at 30 minutes, 24 hours, 48 hours and 72 hours. Multiple dosing regimes gave similar motor and neurocognitive improvements to the single dosing regimen at 20 mg/kg, and possibly an improvement in the MWM performance at 5 or more days. Thus, these experiments demonstrate that Tat-NR2B9c is able to provide neuroprotection and improve motor, cognitive and memory benefits following traumatic brain injuries.

In the Tat-NR2B9c treatment groups, a small hypothermic effect was observed (about 2 degrees C. measured in the rectum) at approximately 90 minutes following PBBI (60 minutes following dosing). This is a potential benefit to patients, because hyperthermia (i.e., a reduction in body temperature responsive to treatment) following stroke or brain injuries is negatively correlated with outcome. Thus, a drug that can reduce the temperature following brain injury is likely to improve outcomes.

Overall, the results indicate that Tat-NR2B9c protects against injury-induced motor abnormalities in the PBBI model with the 0.5 mg/kg dose being the most effective. The 0.5 mg/kg dose of Tat-NR2B9c resulted in significantly improved neuroscore (FIG. 1A) and rotarod performance (FIG. 3A). Tat-NR2B9c also reducing contralateral footfaults on the balance beam (analyzed by beam segment) at 3 days post-injury (see FIG. 2C). Histological analysis of H&E-stained sections, comparing doses of Tat-NR2B9c with PBBI in Study 1 did not reach a significant neuroprotective effect on total lesion volume (FIGS. 4A, B, C). However, there was a trend, particularly in the more caudal sections, providing evidence that Tat-NR2B9c (both doses) was effective in reducing the extent of the lesion (see FIG. 4; lesion progression graph). This trend improved with additional animals tested to demonstrate a 33% reduction in infarct volume in animals treated with 20 mg/kg Tat-NR2B9c. FIGS. 5 and 6 also demonstrate that single or multiple dosing treatments with Tat-NR2B9c protect against learning and cognitive deficits observed after brain injuries. The results constitute evidence that Tat-NR2B9c can provide a therapeutic benefit for penetrative injury to the CNS.

All publications (including GenBank Accession numbers, UniProtKB/Swiss-Prot accession numbers and the like), patents and patent applications cited are herein incorporated by reference in their entirety for all purposes to the same extent as if each individual publication, patent and patent application was specifically and individually indicated to be incorporated by reference in its entirety for all purposes. In the event of any variance in sequences associated with Genbank and UniProtKB/Swiss-Prot accession numbers and the like, the application refers to the sequences associated with the cited accession numbers as of Aug. 12, 2010, the date from which the present application derives priority.

What is claimed is:

1. A method of treating or effecting prophylaxis of a damaging effect of penetrative ballistic injury to the CNS, comprising administering to a subject having or at statistically significant risk of penetrative ballistic injury to the CNS relative to the general population a pharmacological agent that inhibits binding of PSD-95 to an NMDAR and/or of PSD-95 to nNOS at a dose of 0.1 to 10 mg/kg and the administering inhibits development of cognitive deficits in the subject, wherein the pharmacological agent comprises a peptide having an amino acid sequence comprising T/SXV/L linked to an internalization peptide.

2. The method of claim 1, wherein the subject has a gunshot wound in the head.

3. The method of claim 1, wherein the subject is a military or law enforcement person at statistically significant risk of being shot.

4. The method of claim 1, wherein the subject is free of and/or not at statistically significant risk of other diseases amenable to treatment with the pharmacological agent.

5. The method of claim 1, wherein the pharmacological agent comprises a peptide having an amino acid sequence comprising [E/D/N/Q]-[S/THD/E/Q/N]-[V/L] (SEQ ID NO: 38) linked to an internalization peptide.

6. The method of claim 1, wherein the pharmacological agent comprises an internalization peptide linked to a peptide having an amino acid sequence comprising any of ESDV (SEQ ID NO: 12), ESEV (SEQ ID NO: 29), ETDV (SEQ ID NO: 39), ETEV (SEQ ID NO: 40), DTDV (SEQ ID NO: 41), or DTEV (SEQ ID NO: 42) linked to an internalization peptide.

7. The method of claim 1, wherein the pharmacological agent comprises an internalization peptide linked to an amino acid sequence comprising either of KLSSIESDV (SEQ ID NO: 5) or KLSSIETDV (SEQ ID NO: 43) linked to an internalization peptide.

8. The method of claim 1, wherein the internalization peptide is a tat peptide.

9. The method of claim 1, wherein the internalization peptide has an amino acid sequence comprising XGRK-KRRQRRR (SEQ ID NO: 49), wherein X is an amino acid other than Y or nothing.

10. The method of claim 1, wherein X is F (SEQ ID NO:3).

11. The method of claim 1, wherein the pharmacological agent has an amino acid sequence comprising FGYK-KRRQRRRKLSSIESDV (SEQ ID NO:37) or FGYK-KRRQRRRKLSSIETDV (SEQ ID NO: 68).

12. The method of claim 1, wherein the pharmacological agent has an amino acid sequence consisting of FGYK-KRRQRRRKLSSIESDV (SEQ ID NO:37) or FGYK-KRRQRRRKLSSIETDV (SEQ ID NO: 68).

13. The method of claim 1, wherein the pharmacological agent has an amino acid sequence comprising YGRK-KRRQRRRKLSSIESDV (SEQ ID NO: 26) or YGRK-KRRQRRRKLSSIETDV (SEQ ID NO: 69).

14. The method of claim 1, wherein a single dose is administered per episode of penetrative ballistic injury or statistically significant risk thereof.

15. The method of claim 1, wherein the administration is by intravenous infusion.

16. The method of claim 1, further comprising monitoring the subject for neurological deficits from the penetrative injury.

17. The method of claim 16, wherein the monitoring determines cognitive functioning and/or pathology.

18. The method of claim 1, wherein the temperature of the subject is reduced responsive to the administering.

* * * * *